(12) United States Patent
Lau et al.

(10) Patent No.: US 7,976,456 B2
(45) Date of Patent: *Jul. 12, 2011

(54) CARDIAC HARNESS

(75) Inventors: Lilip Lau, Los Altos, CA (US); James Hong, Palo Alto, CA (US); Steven Meyer, Sunnyvale, CA (US); Matthew G. Fishler, Sunnyvale, CA (US); Craig Mar, Fremont, CA (US); Anuja H. Patel, Sunnyvale, CA (US); Sieu Duong, Sunnyvale, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 203 days.

This patent is subject to a terminal disclaimer.

(21) Appl. No.: 12/343,253

(22) Filed: Dec. 23, 2008

(65) Prior Publication Data

US 2009/0156892 A1    Jun. 18, 2009

Related U.S. Application Data

(62) Division of application No. 10/656,722, filed on Sep. 5, 2003, now Pat. No. 7,485,089.

(60) Provisional application No. 60/458,991, filed on Mar. 28, 2003, provisional application No. 60/409,113, filed on Sep. 5, 2002.

(51) Int. Cl.
*A61F 13/00* (2006.01)

(52) U.S. Cl. .......................................... 600/37; 607/129

(58) Field of Classification Search .................... 600/37, 600/16–18; 607/9, 129–132
See application file for complete search history.

(56) References Cited

U.S. PATENT DOCUMENTS 7,225,036 B2 * 5/2007 Lau et al. ...................... 607/129

* cited by examiner

*Primary Examiner* — John P Lacyk
(74) *Attorney, Agent, or Firm* — Fulwider Patton LLP

(57) ABSTRACT

A cardiac harness for treating or preventing congestive heart failure is configured to be placed about at least a portion of a patient's heart so as to apply a mild compressive force on the heart. In one embodiment, the cardiac harness comprises a plurality of spaced apart conductive panels arranged so that there is no electrical continuity circumferentially around the harness. In an additional embodiment, a cardiac harness is provided that is insulated so as not to conduct electricity circumferentially about the harness.

2 Claims, 30 Drawing Sheets

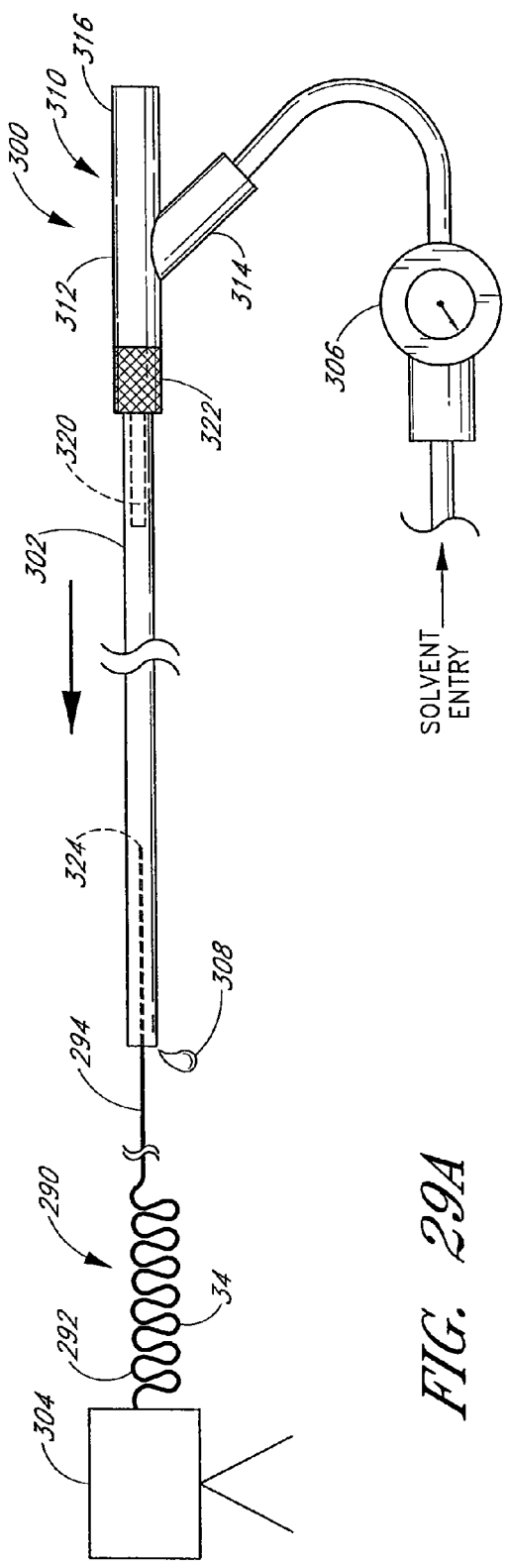
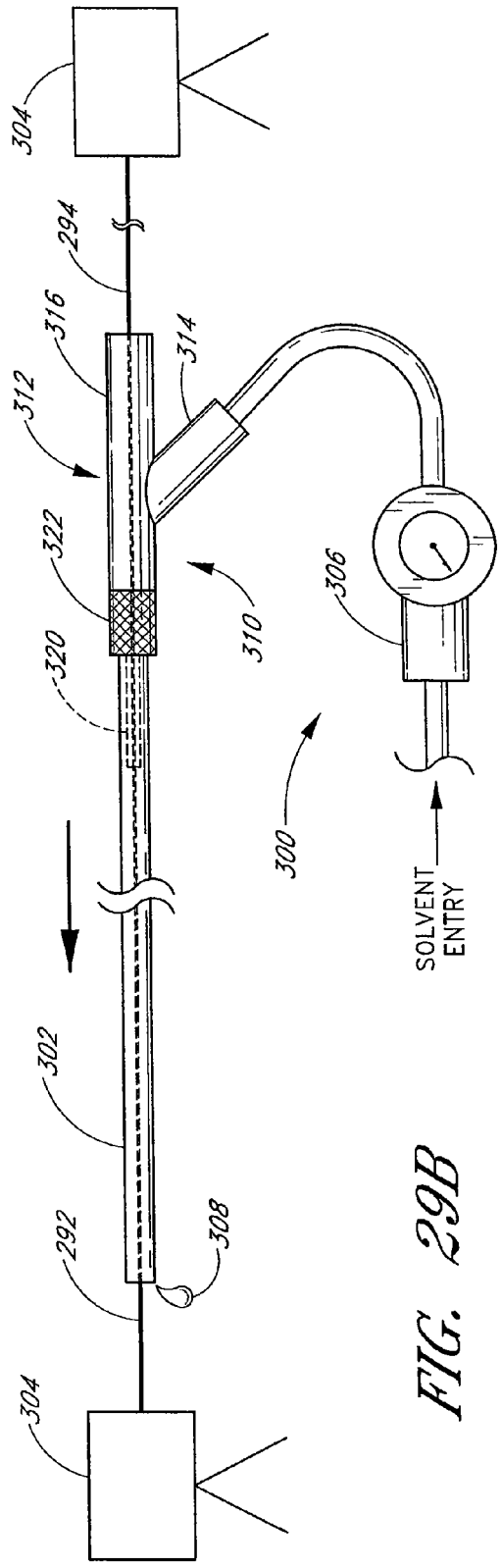
FIG. 29A
FIG. 29B

CARDIAC HARNESS

CROSS-REFERENCES TO RELATED APPLICATIONS

This is a divisional application of U.S. patent application Ser. No. 10/656,722, filed on Sep. 5, 2003 now U.S. Pat. No. 7,485,089, which claims priority from U.S. Provisional Application No. 60/458,991, filed on Mar. 28, 2003, and U.S. Provisional Application No. 60/409,113 filed on Sep. 5, 2002, which are incorporated by reference herein in its entirety.

BACKGROUND

1. Field of the Invention

The present invention relates to a device for treating heart failure. More specifically, the invention relates to a cardiac harness configured to be fit around at least a portion of a patient's heart.

2. Description of the Related Art

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical changes to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a vicious cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

Although some of the above-discussed devices hold promise, there remains a need in the art for an improved device for treating CHF to prevent a remodeled heart from further remodeling and/or help reverse remodeling of a diseased heart.

SUMMARY OF THE INVENTION

In accordance with one embodiment, the present invention provides a cardiac harness configured to fit about a patient's heart. The harness comprises a first panel constructed of a first material and a second panel constructed of a second material that is different than the first material. The first and second panels are positioned adjacent one another. In another embodiment, the first panel is electrically conductive and the second panel is generally electrically non-conductive.

In accordance with another embodiment, the present invention provides a cardiac harness configured to fit about a patient's heart. The harness comprises a plurality of conductive panels. Each of the panels is spaced from an adjacent panel so that there is no electrical continuity between the conductive panels. In still another embodiment, a non-conductive panel is disposed between two adjacent conductive panels.

In another embodiment, a method of manufacturing a cardiac harness comprises providing a flat sheet of conductive material, etching at least one spring member out of the conductive material, and coating the etched spring member with a dielectric material.

In accordance with yet another embodiment, the present invention provides a cardiac harness configured to fit about a patient's heart. The harness comprises a base end, an apex end, a right portion and a left portion. The right portion is configured to be placed generally adjacent a right side of the patient's heart and the left portion is configured to be placed generally adjacent a left side of the patient's heart. A distance between the apex end and the base end in the right portion is greater than a distance between the apex end and the base end in the left portion.

In accordance with a yet further embodiment, a cardiac harness is configured to fit about a patient's heart. The harness comprises a plurality of interconnected spring members comprised of a conductive material. At least some of the spring members are connected to other spring members by a dielectric material such that the dielectric connected spring members are substantially electrically insulated from each other.

In yet another embodiment, a cardiac harness configured to fit about a patient's heart comprises a conductive material. The conductive material is coated with a dielectric coating so as to electrically insulate at least the heart tissue from the conductive material.

In accordance with still another embodiment, a method of manufacturing a cardiac harness comprises providing a metallic wire, covering the wire with a dielectric material, and forming the wire into a plurality of spring members.

In a further embodiment, covering the wire includes introducing a fluid into a tube and sliding the tube over the wire. In yet another embodiment, covering the wire comprises applying the dielectric material to the wire such that the wire is insulated by the dielectric material and removing excess dielectric material from the wire so that the shape of the dielectric material generally follows the shape of the spring members.

In another embodiment, a method of manufacturing a cardiac harness, comprises providing a flat sheet of conductive material, etching at least one spring member out of the conductive material, and coating the etched spring member with a dielectric material.

In yet another embodiment, a cardiac harness is provided which circumferentially surrounds a patient's heart and extends longitudinally from an apex portion to a base portion of the heart. The harness comprises a first portion and a second portion. The first portion is configured to be disposed closer to an apex portion of the heart then the second portion. Further, the first portion comprises a plurality of interconnected panels that are electrically insulated from one another along respective longitudinal sides to inhibit electrical conduction circumferentially about said harness. The second portion is electrically insulated from the first portion.

In yet a further embodiment, a cardiac harness comprises a first spring array and a second spring array. Each spring array comprises a plurality of zig portions interconnected with a plurality of zag portions such that said array is generally zigzag shaped. Each of the zig portions and zag portions comprise a plurality of interconnected spring elements. The first and second spring arrays are connected to one another at a plurality of discrete locations corresponding to interconnections of a zig portion with a zag portion.

In still another embodiment, a cardiac harness is configured to fit about a patient's heart. The harness comprises a plurality of interconnected spring members comprised of a conductive material. At least some of said spring members are connected to other spring members by a dielectric material such that the dielectric connected spring members are substantially electrically insulated from each other.

Further features and advantages of the present invention will become apparent to one of skill in the art in view of the Detailed Description of Preferred Embodiments which follows, when considered together with the attached drawings and claims.

BRIEF DESCRIPTION OF THE DRAWINGS

FIG. 29A shows an apparatus for drawing a tube over a strand, depicted during the process of drawing a tube over the strand of FIG. 28B.

FIG. 29B shows the arrangement of FIG. 29A at a further point in the process of drawing the tube over the strand.

DETAILED DESCRIPTION OF THE PREFERRED EMBODIMENTS

This application relates to a method and apparatus for treating heart failure. As discussed in Applicants' co-pending application entitled "Expandable Cardiac Harness For Treating Congestive Heart Failure", Ser. No. 09/634,043, which was filed on Aug. 8, 2000, the entirety of which is hereby expressly incorporated by reference herein, it is anticipated that remodeling of a diseased heart can be resisted or even reversed by alleviating the wall stresses in such a heart. The present application discusses certain embodiments and methods for supporting the cardiac wall. Additional embodiments and aspects are also and Method", Ser. No. 10/287,723, filed Oct. 31, 2002, and "Method and Apparatus for Supporting a Heart", Ser. No. 10/338,934, filed Jan. 7, 2003, the entirety of each of which are hereby expressly incorporated by reference.

Figure 1:
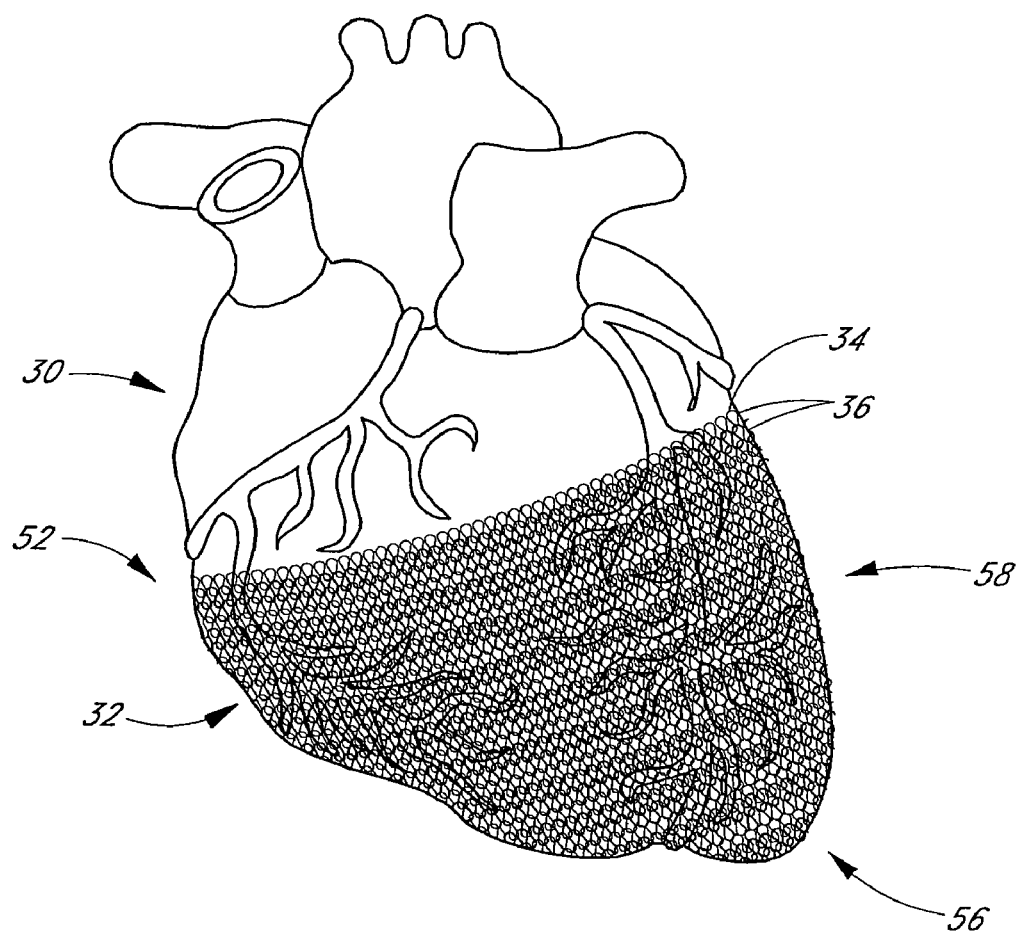
FIG. 1 is a schematic view of a heart with cardiac harness placed thereon.

FIG. 1 illustrates a mammalian heart 30 having a cardiac wall stress reduction device in the form of a harness 32 applied to it. The cardiac harness 32 comprises a series of hinges or spring elements 34 that circumscribe the heart 30 and, collectively, apply a mild compressive force on the heart so as to alleviate wall stresses.

The term "cardiac harness" as used herein is a broad term that refers to a device fit onto a patient's heart to apply a compressive force on the heart during at least a portion of the cardiac cycle. Other devices that are intended to be fit onto a heart and are referred to in the art as "girdles," "socks," "jackets," or the like are included within the meaning of "cardiac harness."

Figure 2A:
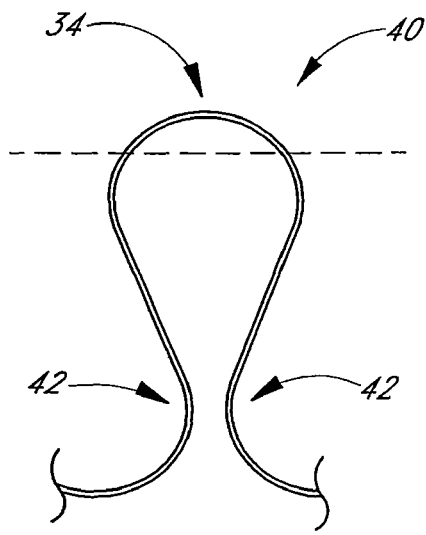
FIGS. 2A-2B illustrate a spring hinge in a relaxed position and under tension.
Figure 2B:
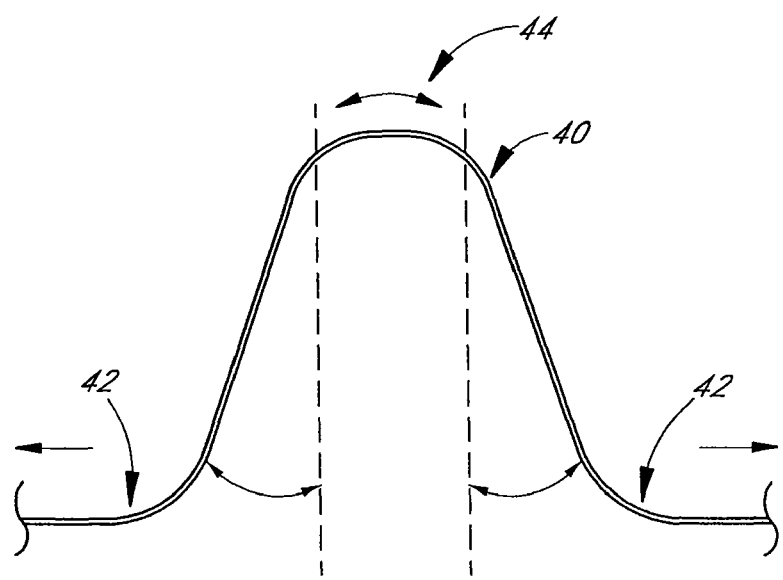

The cardiac harness 32 illustrated in FIG. 1 comprises at least one undulating strand 36 comprising a series of spring elements 34 referred to as hinges or spring hinges that are configured to deform as the heart 30 expands during filling. Each hinge 34 provides substantially unidirectional elasticity, in that it acts in one direction and does not provide much elasticity in the direction perpendicular to that direction. For example, FIG. 2A shows one embodiment of a hinge member 34 at rest. The hinge member 34 has a central portion 40 and a pair of arms 42. As the arms are pulled, as shown in FIG. 2B, a bending moment 44 is imposed on the central portion 40.

The bending moment 44 urges the hinge member 34 back to its relaxed condition. Note that a typical strand comprises a series of such hinges, and that the hinges 34 are adapted to elastically expand and retract in the direction of the strand 36.

In the embodiment illustrated in FIG. 1, the strands 36 of spring elements 34 are constructed of extruded wire that is deformed to form the spring elements. Although FIG. 1 shows adjacent strands 36 interwoven one with another, it is to be understood that, in additional embodiments, adjacent strands 36 may not overlay or touch one another.

Figure 3:
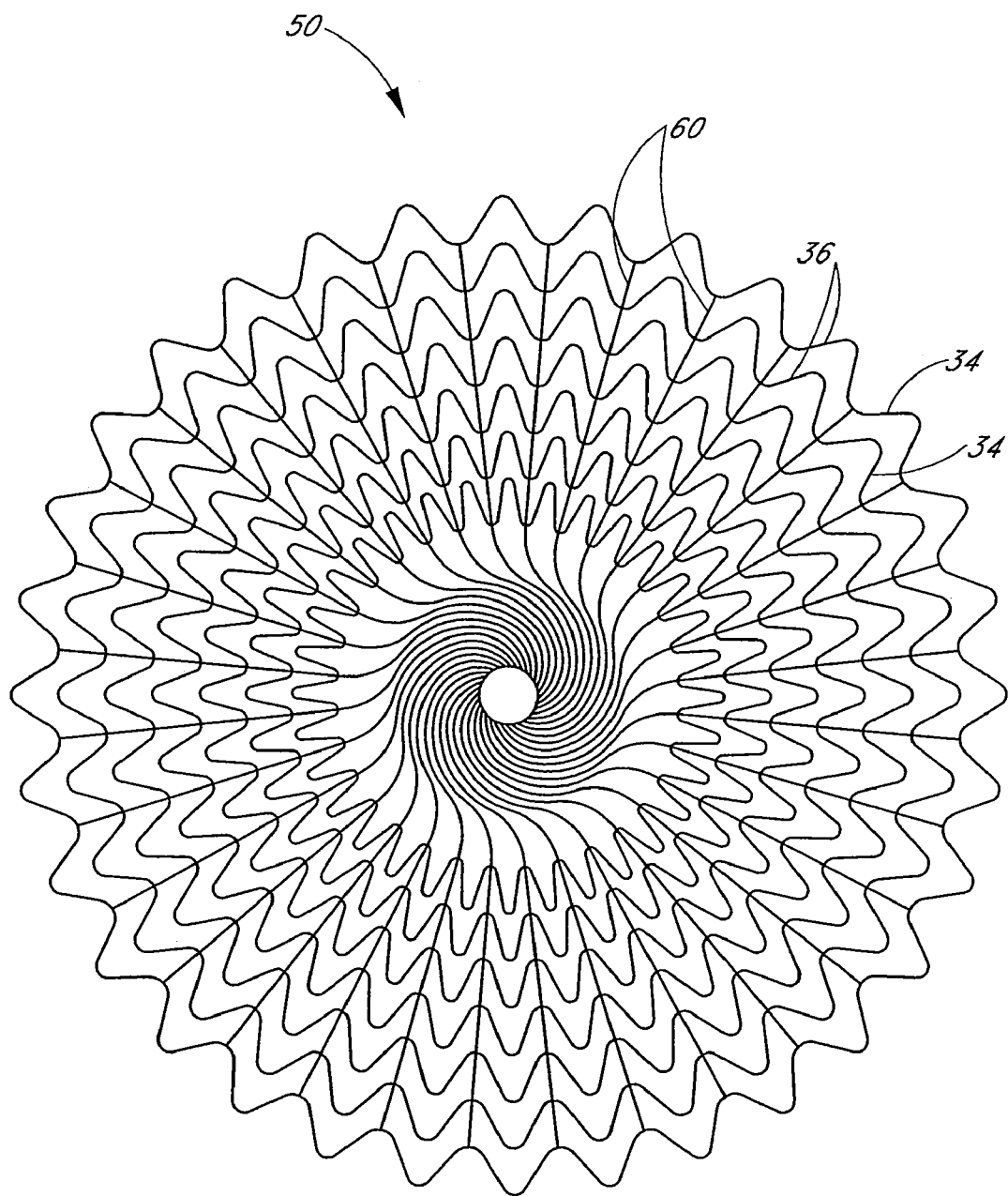
FIG. 3 shows an embodiment of a cardiac harness that has been cut out of a flat sheet of material.
Figure 4:
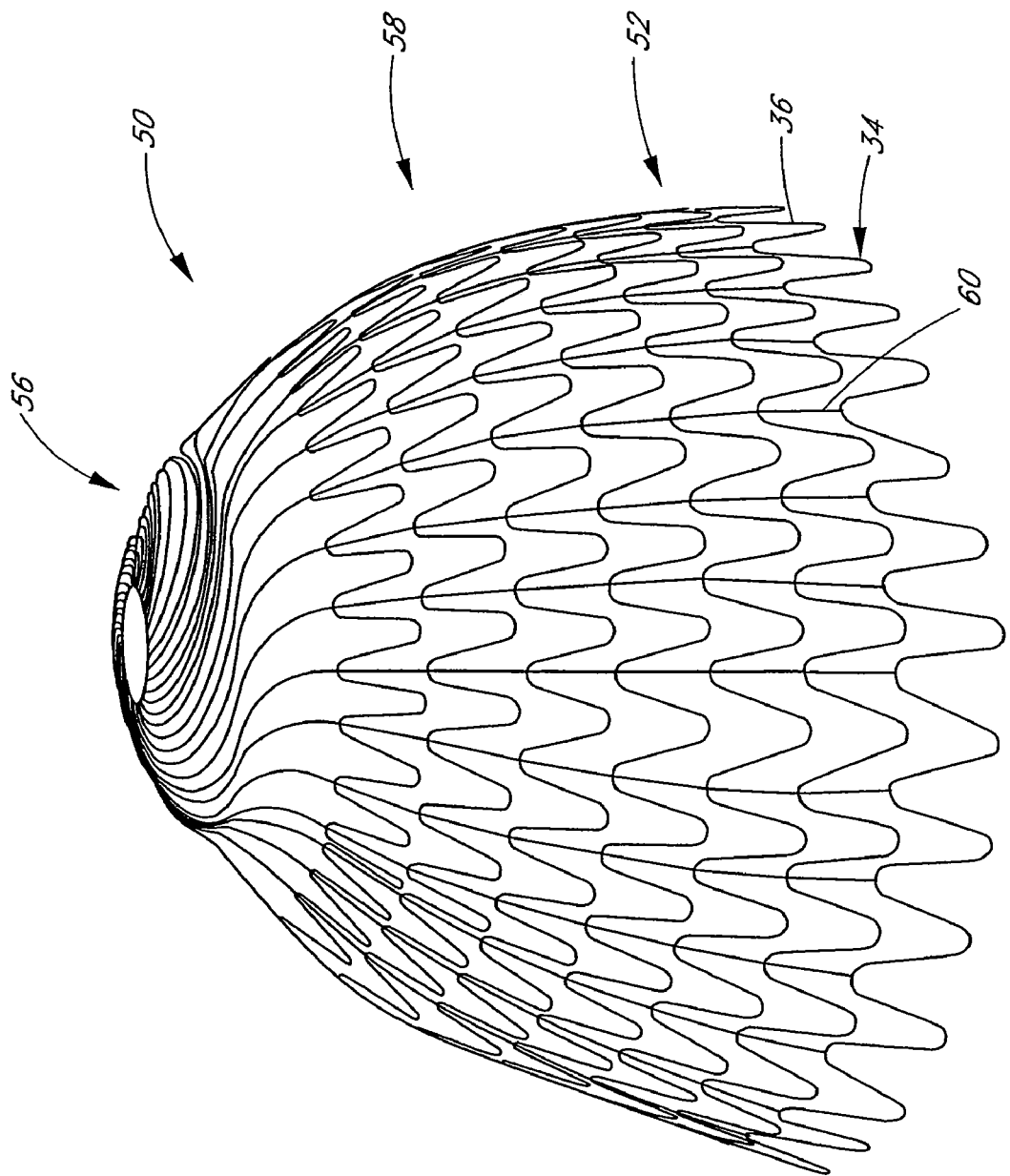
FIG. 4 shows the cardiac harness of FIG. 3 formed into a shape configured to fit about a heart.

FIGS. 3 and 4 illustrate another preferred embodiment of a cardiac harness 50, shown at two points during manufacture of such a harness. In the illustrated embodiment, the harness 50 is first formed from a relatively thin, flat sheet of material. Any method can be used to form the harness from the flat sheet. For example, in one embodiment, the harness is photochemically etched from the material; in another embodiment, the harness is laser-cut from the thin sheet of material. The embodiment shown in FIGS. 3 and 4 has been etched from a thin sheet of Nitinol, which is a superelastic material that also exhibits shape memory properties. The flat sheet of material is draped over a form, die or the like, and is formed to generally take on the shape of at least a portion of a heart.

With reference to FIGS. 1 and 4, the illustrated embodiments of the cardiac harnesses 32, 50 comprise a base portion 52, which is sized and configured to generally engage and fit onto a base region of a patient's heart; an apex portion 56, which is sized and shaped so as to generally engage and fit on an apex region of a patient's heart; and a medial portion 58 between the base and apex portions.

In the embodiment shown in FIGS. 3 and 4, the harness 50 comprises strands or rows 36 of undulating wire. As discussed above, the undulations comprise hinges/spring elements 34 which are elastically bendable in a desired direction. Some of the strands 36 are connected to each other by interconnecting elements 60. The interconnecting elements 60 help maintain the position of the strands 36 relative to one another. Preferably the interconnecting elements 60 allow some relative movement between adjacent strands 36.

As discussed above, and as discussed in more detail in the applications that are incorporated herein by reference, the undulating spring elements 34 exert a force in resistance to expansion of the heart 30. Collectively, the force exerted by the spring elements tends toward compressing the heart, thus alleviating wall stresses in the heart as the heart expands. Accordingly, the harness helps to decrease the workload of the heart, enabling the heart to more effectively pump blood through the patient's body and enabling the heart an opportunity to heal itself. It should be understood that several arrangements and configurations of spring members can be used to create a mildly compressive force on the heart so as to reduce wall stresses. For example, spring members can be disposed over only a portion of the circumference of the heart or harness.

Figure 5:
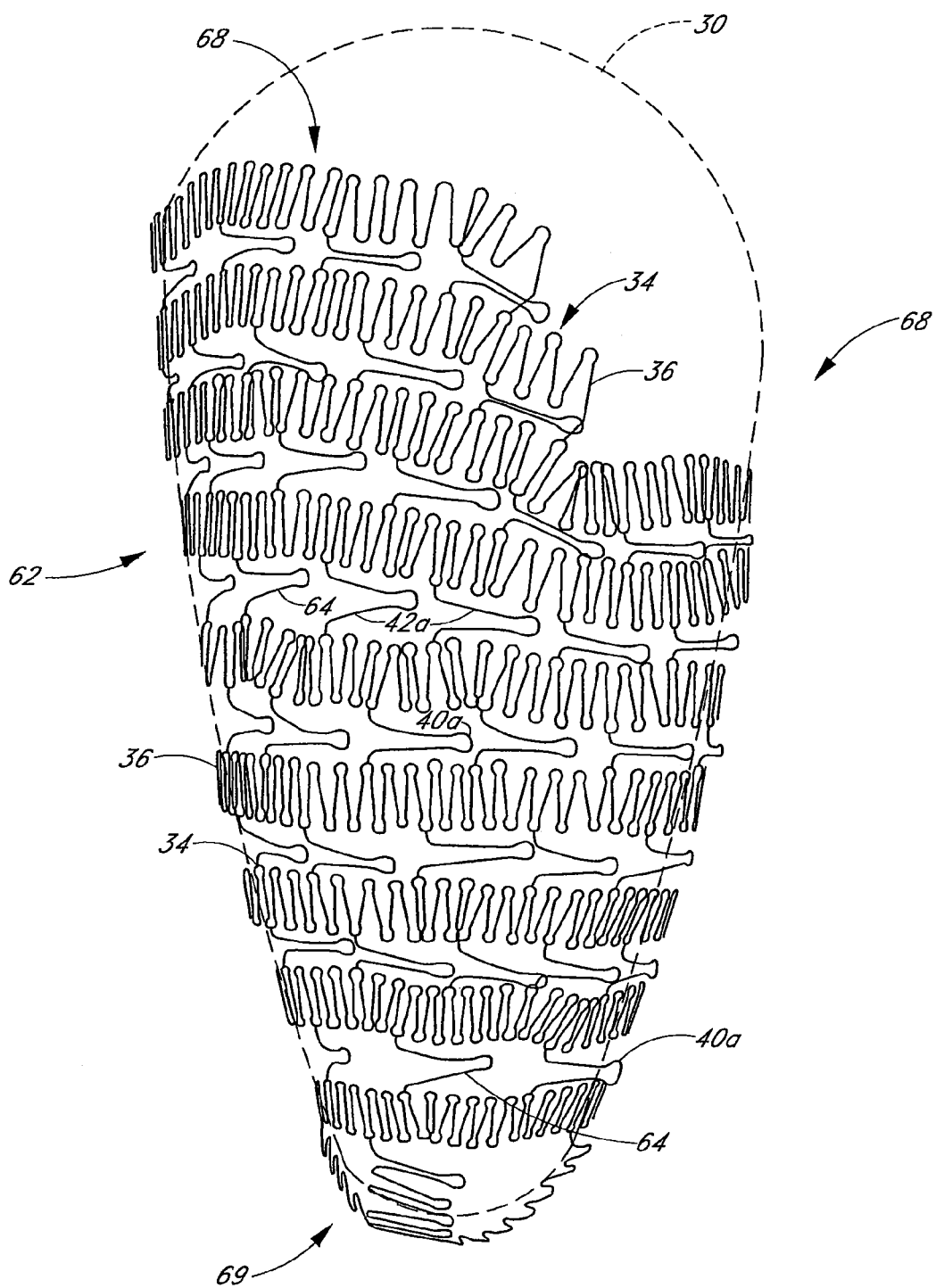
FIG. 5 shows another embodiment of a cardiac harness in place on a schematically illustrated heart.
Figure 6:
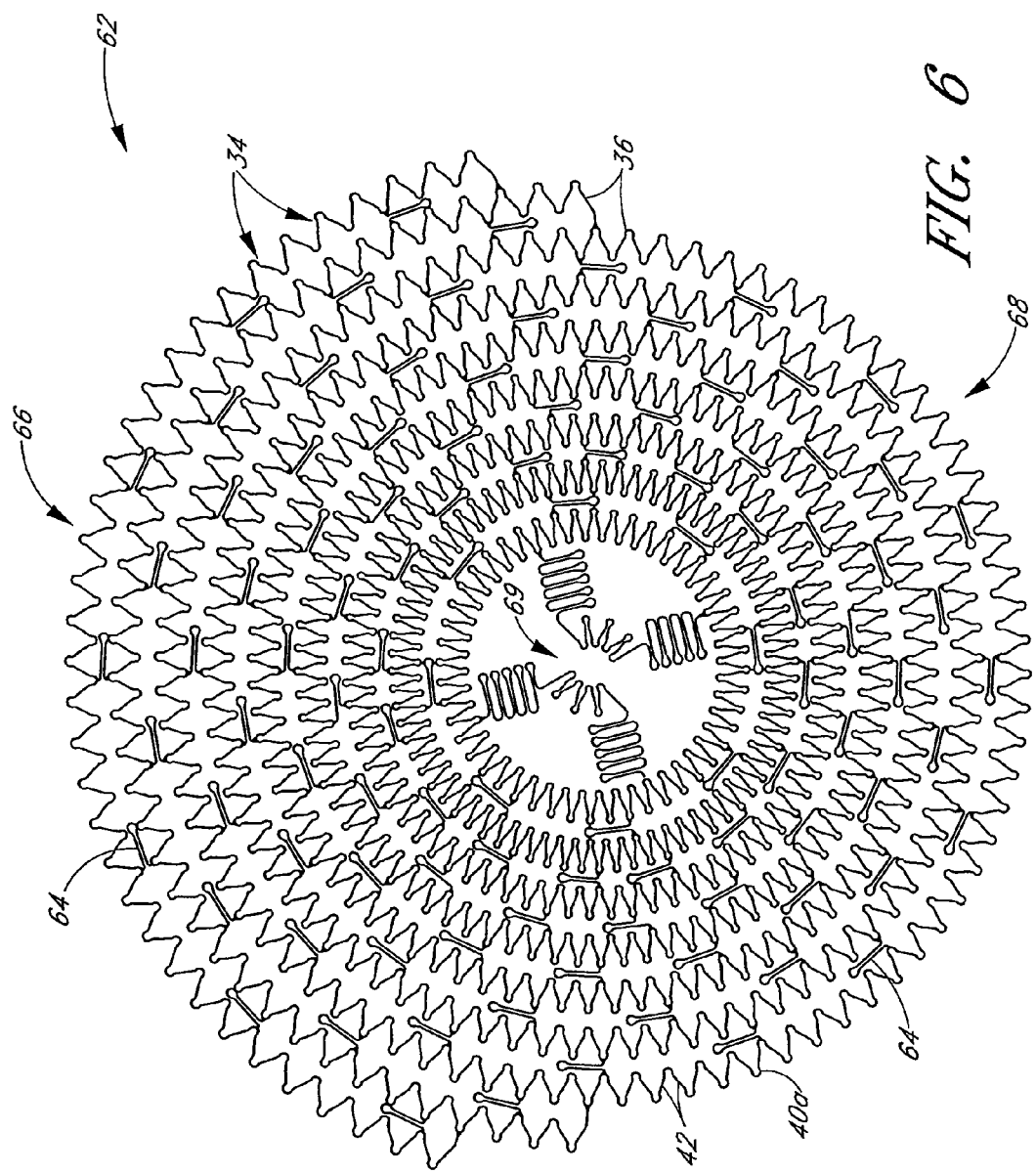
FIG. 6 shows the cardiac harness embodiment of FIG. 5 in a flat state before being formed to fit onto a heart.
Figure 7:
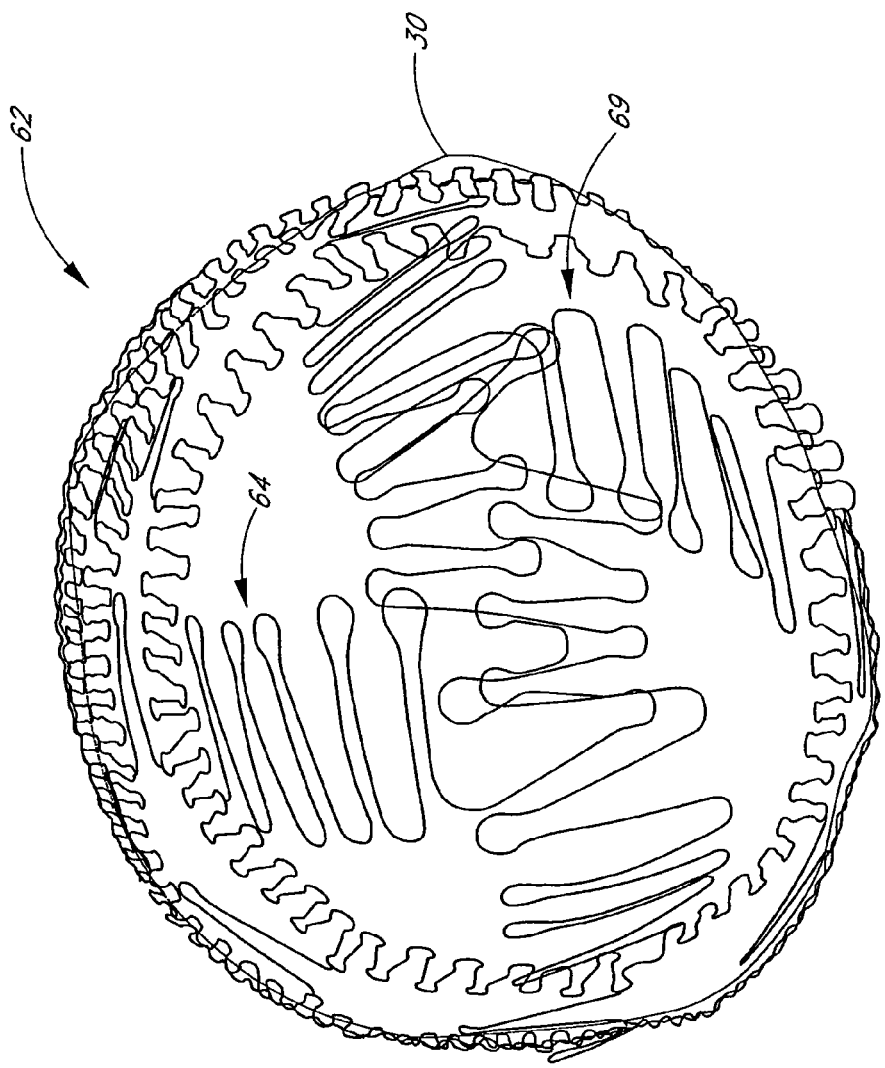
FIG. 7 shows the arrangement of FIG. 5 as viewed looking toward an apex of the heart.

With reference to FIGS. 5 through 7, another embodiment of a cardiac harness 62 is illustrated. FIG. 5 shows the harness 62 disposed upon a simulated heart 30. As shown, the harness fits circumferentially about the heart.

With specific reference next to FIGS. 5 and 6, the illustrated embodiment comprises several rows/strands 36 of undulating spring hinges 34. As shown, the spring hinges each have a "keyhole" shape. As with the hinges 34 discussed above with reference to FIG. 2, each keyhole-shaped hinge comprises two elongate arms 42 connected by a central portion 40a. The central portion 40a generally is accurate about a radius. In one preferred embodiment the arcuate central portion generally extends more than about 180 degree. about the radius. As such, bending stresses are distributed through the whole central portion 40a during stretching of each spring hinge.

With continued reference to FIGS. 5-7, each row or strand 36 of spring hinges 34 is attached to an adjacent row or strand of spring hinges by one or more longitudinally-extending spring hinges 64. In the illustrated embodiment, each of the longitudinal spring hinges 64 are of the keyhole shape and comprise a pair of arms 42a and an arcuate central portion 40a. In the illustrated embodiment, the arms 42a of the longitudinal hinges 64 are generally longer than those of the circumferential spring hinges 34 and thus are more relaxed and compliant. Accordingly, the resistance of the harness 62 to expansion in a longitudinal direction of the heart is considerably less than resistance of the harness to circumferential expansion of the heart. In a preferred embodiment, the longitudinal spring hinges 64 of the harness 62 collectively are very compliant and offer little or no resistance to longitudinal elongation. The longitudinal spring hinges serve to maintain proper alignment between circumferential strands of hinges. As shown in FIG. 5, the longitudinal spring hinges 64 allow adjacent rows 36 of circumferential spring hinges 34 to adjust position relative to one another while maintaining the integrity of the overall shape of the harness 62.

With specific reference to FIGS. 5 and 6, a right side 66 of the harness 62 comprises more rows/strands of hinges than a left side 68 of the harness 62. As such, the harness 62 extends higher on the right side of the heart than on the left side of the heart. Due to the anatomy of the human heart, the right ventricle of the heart extends further from the apex of the heart than does the left ventricle. The harness 62 illustrated in FIGS. 5 and 6 fits about the top of the right ventricle where the ventricle begins to curve inwardly. As such, the harness fits better and is held more securely on the heart than if the right side 66 of the harness 62 were the same as the left 68.

With specific reference to FIGS. 6 and 7, the apex portion 69 of the harness 62 comprises a plurality of longitudinal spring hinges 64. When the device is installed on a heart 30, as shown in FIG. 7, adjacent spring hinges 64 may overlap one another. However, the spring hinges remain very compliant. This arrangement allows significant motion of the apex of the heart in any direction with very little, if any, resistance from the harness 62. In order to help maintain the position of the harness on the heart, one or more sutures can optionally be applied to the heart at the apex in order to hold the overlapping spring hinges in place.

As the heart expands and contracts during diastole and systole, the contractile cells of the myocardium expand and contract. In a diseased heart, the myocardium may expand such that the cells are distressed and lose at least some contractility. Distressed cells are less able to deal with the stresses of expansion and contraction. As such, the effectiveness of heart pumping decreases. Each series of spring hinges of the above cardiac harness embodiments is configured so that as the heart expands during diastole the spring hinges correspondingly will expand, thus storing expansion forces as bending energy in the spring. As such, the stress load on the myocardium is partially relieved by the harness. This reduction in stress helps the myocardium cells to remain healthy and/or regain health.

It is to be understood that several embodiments of cardiac harnesses can be constructed and that such embodiments may have varying configurations, sizes, flexibilities, etc. As discussed in the above-referenced applications, such cardiac harnesses can be constructed from many suitable materials including various metals, fabrics, plastics and braided filaments. Suitable materials also include superelastic materials and materials that exhibit shape memory. For example, a preferred embodiment is constructed of Nitinol. Shape memory polymers can also be employed. Such shape memory polymers can include shape memory polyurethanes or other polymers such as those containing oligo (e-caprolactone) dimethacrylate and/or poly(e-caprolactone), which are available from mnemoScience.

As just discussed, bending stresses are absorbed by the spring members 34 during diastole and are stored in the members as bending energy. During systole, when the heart pumps, the heart muscles contract and the heart becomes smaller. Simultaneously, bending energy stored within the spring members 34 is at least partially released, thereby providing an assist to the heart during systole. In a preferred embodiment, the compressive force exerted on the heart by the spring members of the harness comprises about 10% to 15% of the mechanical work done as the heart contracts during systole. Although the harness is not intended to replace ventricular pumping, the harness does substantially assist the heart during systole.

Diseased hearts often have several maladies. One malady that is not uncommon is irregularity in heartbeat caused by irregularities in the electrical stimulation system of the heart. For example, damage from a cardiac infarction can interrupt the electrical signal of the heart. In some instances, implantable devices, such as pacemakers, help to regulate cardiac rhythm and stimulate heart pumping. A problem with the heart's electrical system can sometimes cause the heart to fibrillate. During fibrillation, the heart does not beat normally, and sometimes does not pump adequately. A cardiac defibrillator can be used to restore the heart to normal beating. A defibrillator typically includes a pair of electrode paddles applied to the patient's chest. The defibrillator generates an electric field between electrodes. An electric current passes through the patient's heart and stimulates the heart's electrical system to help restore the heart to regular pumping.

Sometimes a patient's heart begins fibrillating during heart surgery or other open-chest surgeries. In such instances, a special type of defibrillating device is used. An open-chest defibrillator includes special electrode paddles that are configured to be applied to the heart on opposite sides of the heart. A strong electric field is created between the paddles, and an electric current passes through the heart to defibrillate the heart and restore the heart to regular pumping.

In some patients that are especially vulnerable to fibrillation, an implantable heart defibrillation device may be used. Such an implantable device generally includes one or more electrodes mounted directly on, in or adjacent the heart wall. If the patient's heart begins fibrillating, these heart-mounted electrodes will generate an electric field therebetween in a similar manner as the other defibrillators discussed above.

Testing has indicated that when defibrillating electrodes are applied to a heart that is surrounded by a device made of electrically conductive material, at least some of the electrical current disbursed by the electrodes is conducted around the heart by the conductive material, rather than through the heart. Thus, the efficacy of defibrillation is reduced. Accordingly, Applicants have developed several cardiac harness embodiments that enable defibrillation of the heart without conducting electrical current around the heart through the harness.

Figure 8:
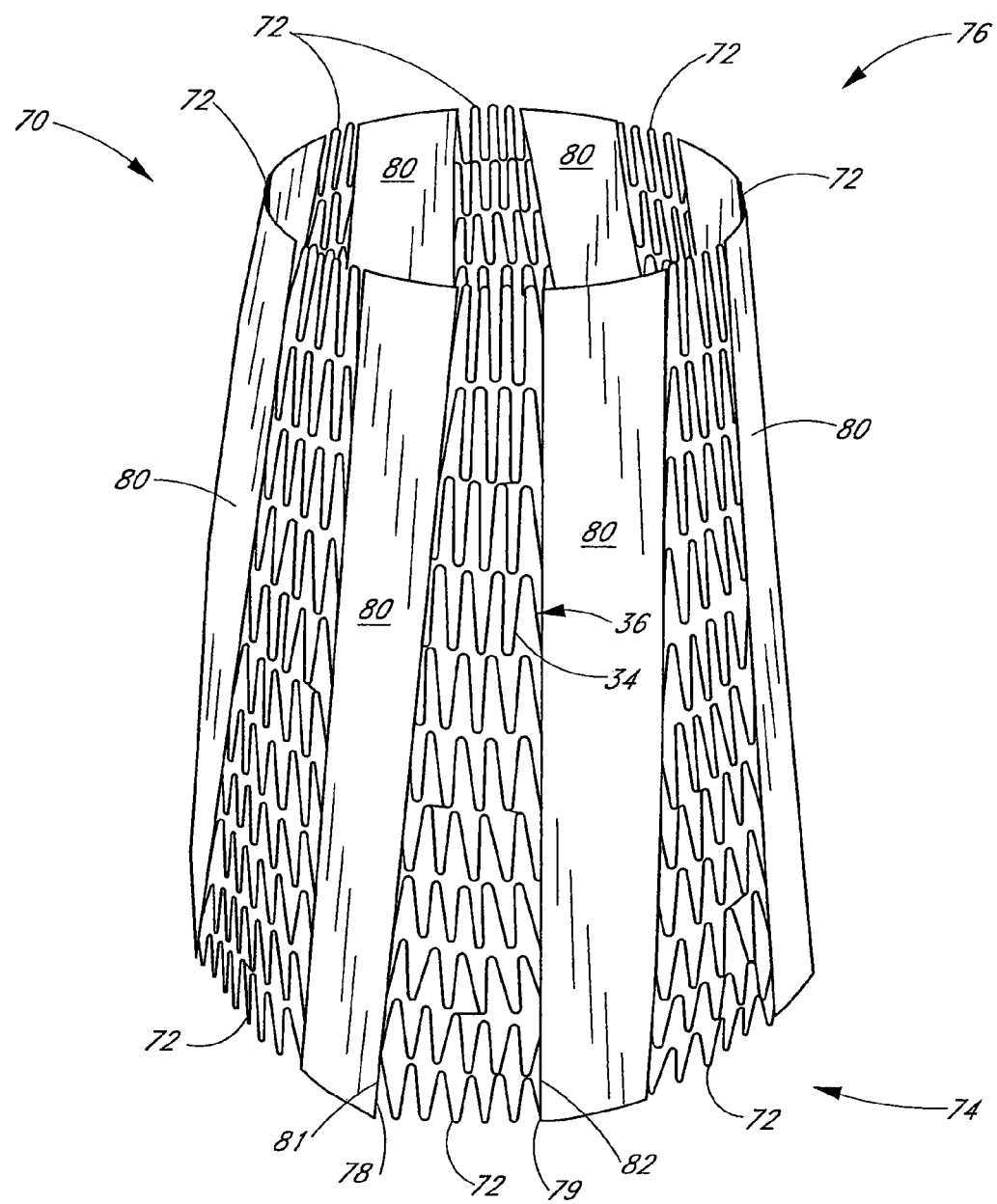
FIG. 8 schematically illustrates another embodiment of a cardiac harness.

With next reference to FIG. 8, another embodiment of a cardiac harness 70 is presented wherein the harness 70 comprises several panels. An elongate spring hinge panel 72 extends generally longitudinally from the base end 74 to the apex end 76 of the harness 70, and transversely over only a portion of the circumference of the harness 70. In the illustrated embodiment, the distance from a first side edge 78 to a second side edge 79 of the panel 73 comprises about 10-50 degrees about the circumference of the harness 70.

The spring hinge panel 72 comprises several interconnected rows of spring hinge strands 36. Each strand comprises a series of spring hinges 34 that are configured to expand and contract generally in a transverse direction relative to a longitudinal axis of the harness 70. In the illustrated embodiment, the strands are constructed of a metallic material, such as Nitinol. As such, the spring hinge panel 72 is generally conductive.

A nonconductive panel 80 is disposed adjacent the spring hinge panel 72. The nonconductive panel 80 also extends from the base end 74 to the apex end 76 of the harness 70, and has a first side edge 81 that is connected to the adjacent spring hinge panel 72. A second side edge 82 of the nonconductive panel 80 is connected to another spring hinge panel 72.

In the cardiac harness illustrated in FIG. 8, eight spring hinge panels 72 are provided, and each spring hinge panel is separated from adjacent spring hinge panels by a nonconductive panel 80. Thus, each spring hinge panel 72 is electrically isolated from the other spring hinge panels in the harness 70. This arrangement ensures that there is no electrical continuity circumferentially about the harness 70. Thus, if defibrillator paddles are applied to a harness that is placed on the patient's heart, the electrical field created between the paddles cannot be conducted around the heart through the harness. Instead, the electrical field passes through the heart, and the effectiveness of the defibrillating paddles is not defeated by the presence of the harness.

In the illustrated embodiment, the nonconductive panels 80 each comprise a layer of polymer that is connected to portions of each adjacent spring hinge panel 72 by adhesive or any other mode of connection. Preferably, each nonconductive panel 80 preferably is generally inelastic or has relatively low elasticity so that the elastic expansion and contraction of the harness is generally controlled by the properties of the spring hinge panels. Of course, in additional embodiments, at least one nonconductive panel can be formed of an elastic material that contributes significantly to the expansion of the harness and the mild compressive force applied to the heart by the harness.

The harness 70 illustrated in FIG. 8 comprises eight conductive spring hinge panels 72 and eight nonconductive panels 80. It is to be understood that, in other embodiments, any number of panels can be used to break the electrical continuity circumferentially around the harness. For example, harnesses having 2, 3, 4 or more panels can advantageously be employed to break electrical continuity. In addition, the size of the nonconductive panels can be adjusted. For example, in the embodiment illustrated in FIG. 8, each of the nonconductive panels 80 from the first edge 81 to the second edge 82 comprise about 10-20 degrees about the circumference of the harness 70. It is to be understood that other angular dimensions, such as between about 25 to 55 degrees, 35-45 degrees, and even about 10 to 90 degrees can be acceptable.

As a general rule, the greater the angular width of the nonconductive panels 80, the fewer the number of panels that should be used to obtain a desired circumferential electrical discontinuity. Still further, placement of the harness 70 on the heart further affects the effectiveness of the panel in controlling electrical continuity. For example, in a preferred embodiment, the harness is placed upon the heart so that at least one nonconductive panel 80 on each side of the heart is disposed between advantageous placement locations of the defibrillator paddles.

Figure 9:
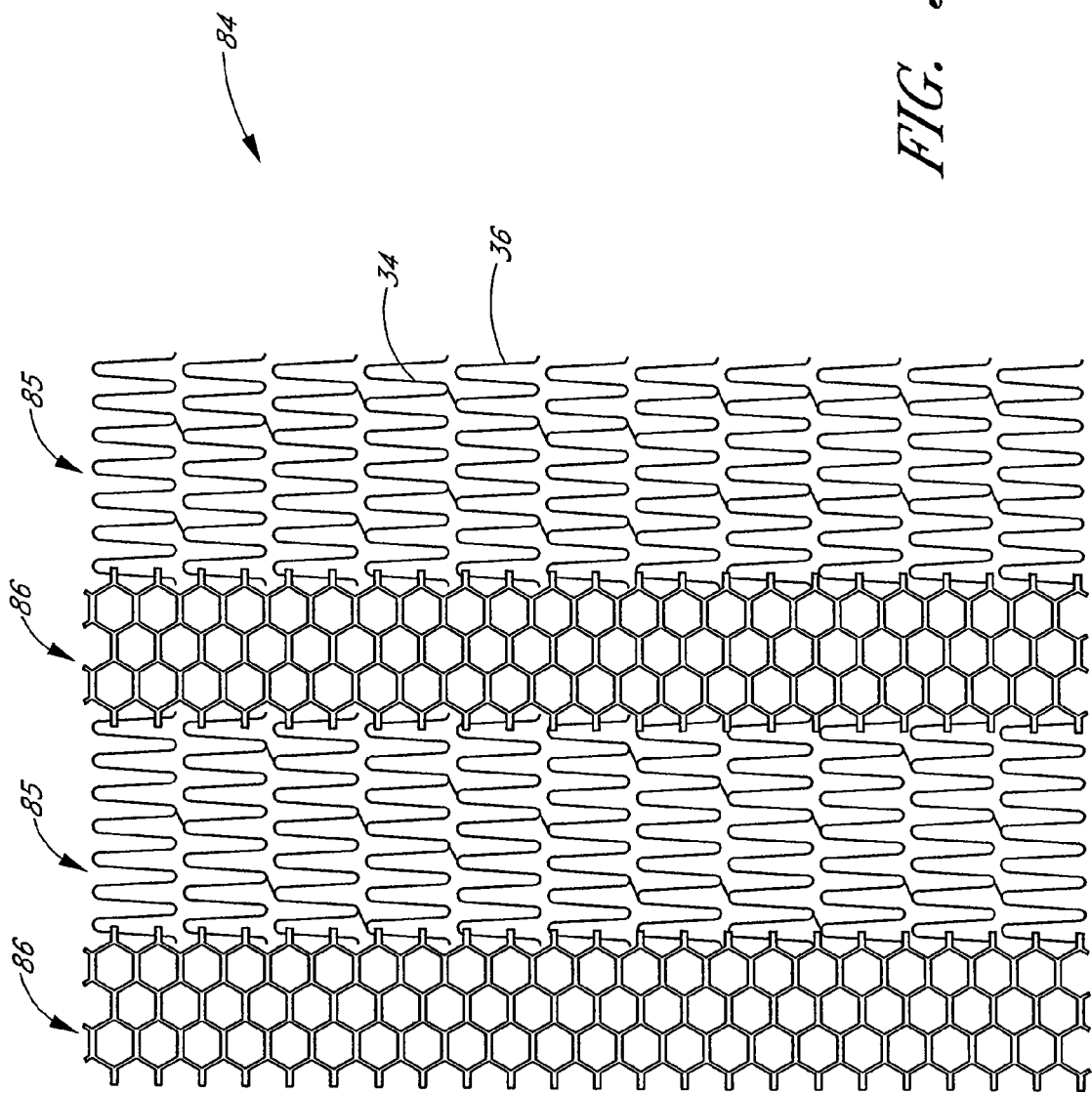
FIG. 9 schematically illustrates a portion of still another embodiment of a cardiac harness.

With specific reference to FIG. 9, a portion of another embodiment of a cardiac harness 84 is provided comprising spring hinge panels 85 separated by nonconductive panels 86 constructed of a polyester knit material. In the illustrated embodiment, the panels 85, 86 are shown schematically, prior to being formed into a harness shape. In the illustrated embodiment, the polyester knit panel 86 comprises polyester filaments knit in a well known "Atlas knit" arrangement, such as that discussed in International patent Publication Number WO 01/95830A2, which is incorporated herein by reference in its entirety. As such, the panel 86 is flexible, and the fabric can stretch, even though the polyester filaments do not necessarily elastically deform upon stretching of the fabric. Such fabric stretch is mainly due to linearization of filaments and fiber crimp and geometric distortion of the knit pattern. Once these stretch factors are exhausted, the panel 86 becomes inelastic, and will no longer expand elastically with an increase in size of a patient's heart. As such, the circumferential expansion and contraction of the harness preferably is controlled by the spring hinge panels 85. Even if the polyester knit is stretched to its limit so that it cannot stretch further elastically with an increase in the size of a patient's heart, the spring hinge panels 85 are configured so that they will continue to circumferentially expand with the heart so that no elastic limit of the spring hinge panels is reached within the operating range of the device.

In the illustrated embodiment, the polyester knit panel 86 is connected to adjacent spring hinge panels 85 by any suitable means. For example, the polyester knit can be melted or molded onto an edge or adjacent to an edge of a spring hinge panel. Additionally, the polyester knit can be looped around a portion of a spring hinge panel and tied or heat molded onto itself. Still further methods and apparatus for connecting a nonconductive panel to a conductive spring hinge panel will be discussed below.

Of course, it is to be understood that several types of polymer materials can acceptably be used, whether in sheet, knit, mesh or other form, to form a non-conductive panel. For example, any medical grade polymer can be acceptable, including, for example, polyethylene, polypropylene, polyurethanes, nylon, PTFE and ePTFE.

In another embodiment, at least one nonconductive panel comprises a spring hinge panel that has been coated with a dielectric material so as to be electrically insulated from adjacent, conductive spring hinge panels. In a still further embodiment, each of the panels may comprise such insulated spring hinge panels. As such, the panels retain their advantageous spring hinge properties, but electricity is prevented from flowing between panels even if a portion of the insulation about one or more panels degrades or fails.

The multi-panel construction discussed above lends itself to various methods of use and operation. For example, panels of varying material properties and characteristics can be combined to increase the versatility of a cardiac harness. More specifically, for example, a first spring hinge panel comprising a series of spring hinges having a first level of compliance can be connected adjacent a nonconductive, low elasticity panel which, in turn, is connected to a second spring hinge panel which is configured to have a second level of compliance that is greater than the compliance of the first spring hinge panel. The multi-panel harness thus can be customized to both manage electrical conductivity and provide custom-tailored support to specific portions of the heart. For example, the less compliant first spring hinge panel may be applied over a portion of a patient's heart known to have been damaged by a previous infarction; this portion of the heart benefits from the extra support. Meanwhile, the more compliant second spring hinge panel is applied to more healthy portions of the patient's heart which require less support. In another example, the less compliant first panel can be positioned adjacent a left ventricle and the more compliant second panel can be positioned adjacent a right ventricle. The larger, harder-working left ventricle benefits from the extra support, while the right ventricle benefits from the less-restrictive support. It is to be understood, however, that the spring hinge panels remain more compliant than the heart wall.

Figure 10:
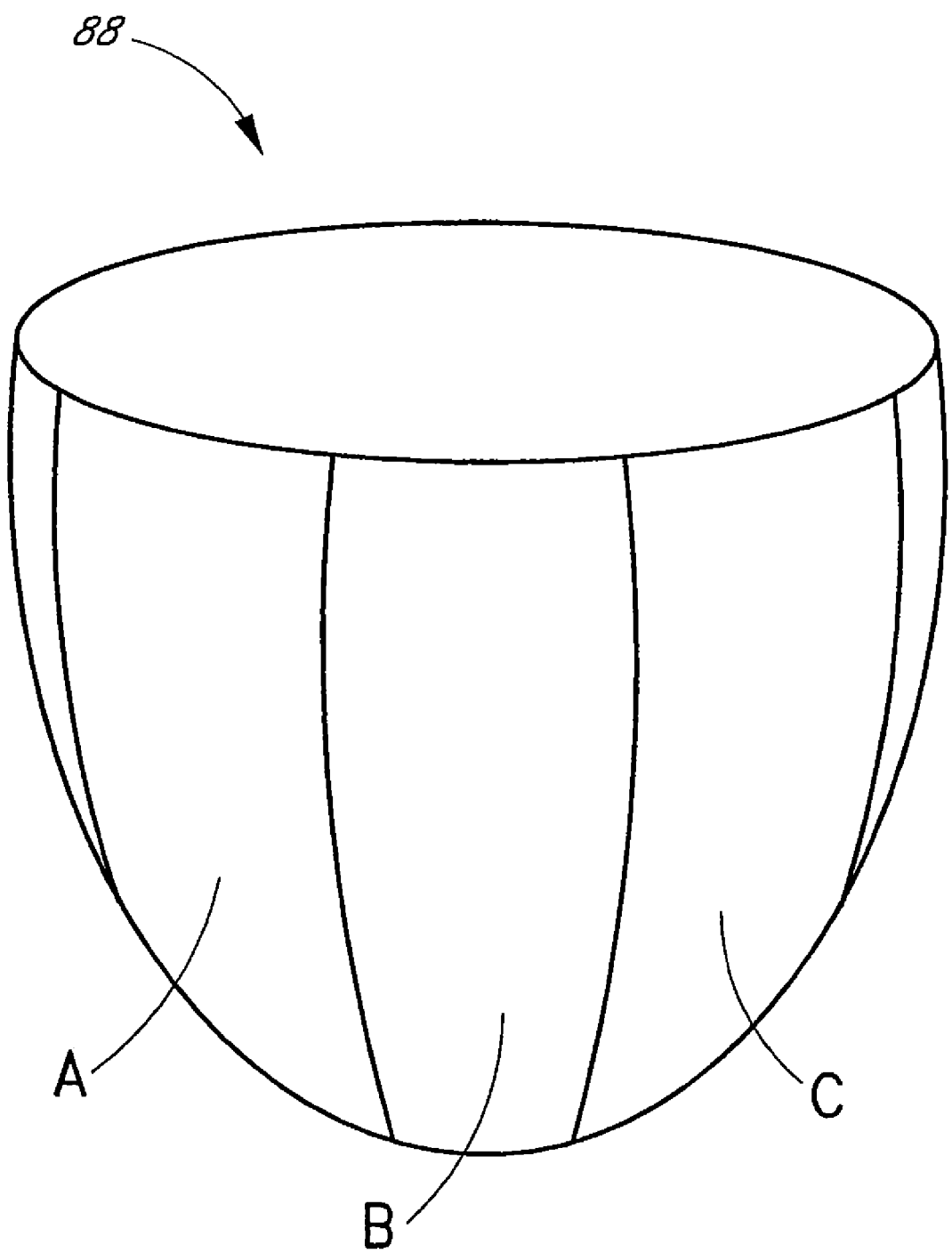
FIG. 10 schematically represents a multi-panel cardiac harness.

In further embodiments, several different types of panels can be assembled together to form a harness. For example, certain panels of the cardiac reinforcement device may have a pacemaking or defibrillating function. FIG. 10 schematically shows an embodiment of a cardiac harness 88 having a plurality of panels each having different characteristics. Panels A, B and C each have different characteristics, be they differences in electrical conductivity, elasticity, or in operational role. For example, in one embodiment panel A is a spring hinge panel; panel B is a nonconductive panel; and panel C is an electrical control panel that comprises a series of sensors and/or leads. Such sensors detect certain types of electrical activity in the heart and relay such sensed activity to a microprocessor. Upon instructions from the processor, the leads deliver an electric charge in order to defibrillate the heart, if needed, or to help pace the heart.

It is to be understood that additional sensor/lead arrangements can be employed. For example, in additional embodiments, one or more of the nonconductive panels can include leads and/or sensors. Further, one or more of the spring hinge panels can includes such leads and/or sensors. Still further, leads and/or sensors can be disposed on both nonconductive and conductive panels.

Figure 11:
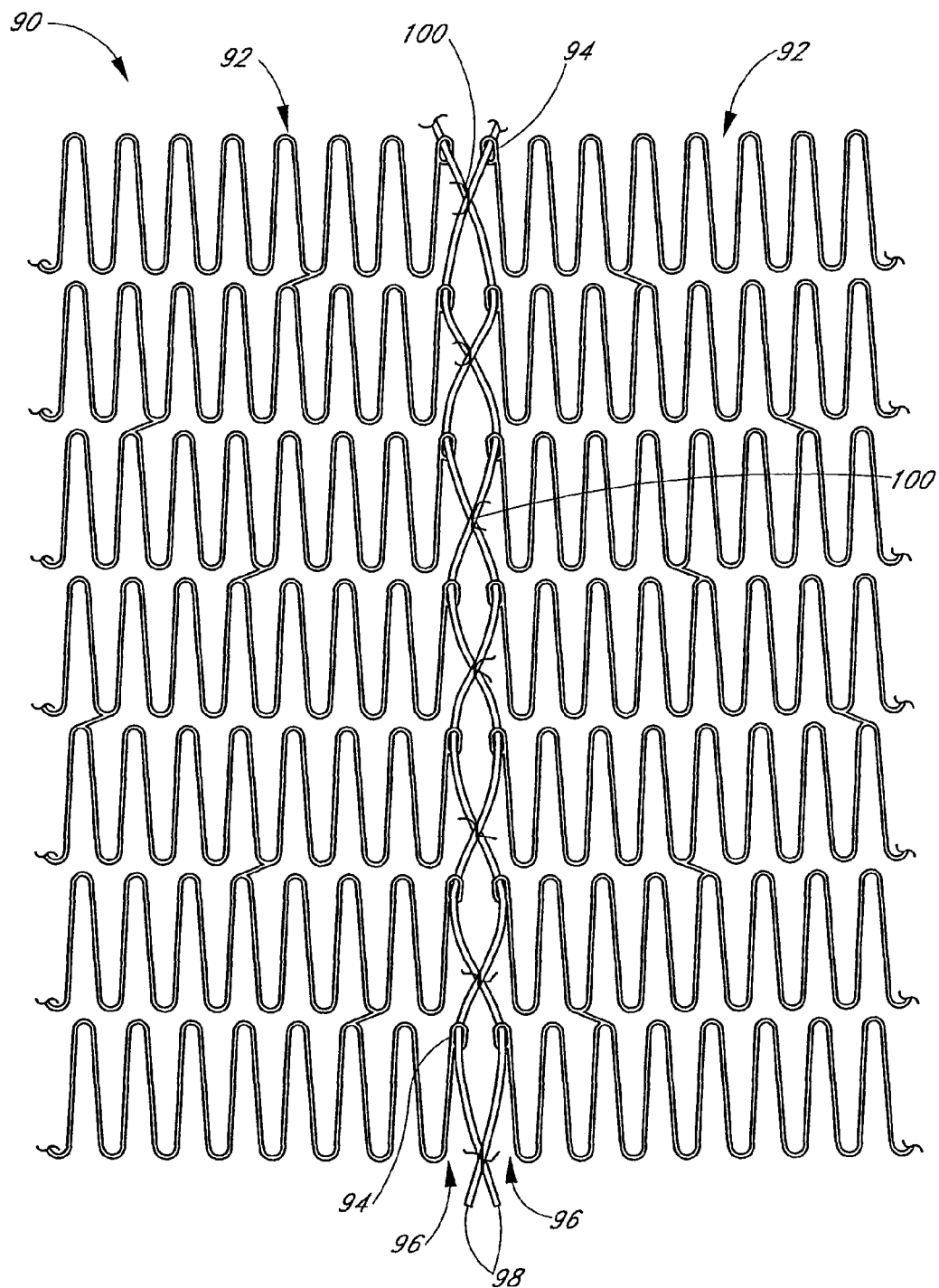
FIG. 11 illustrates a portion of a still further embodiment of a cardiac harness.
Figure 12:
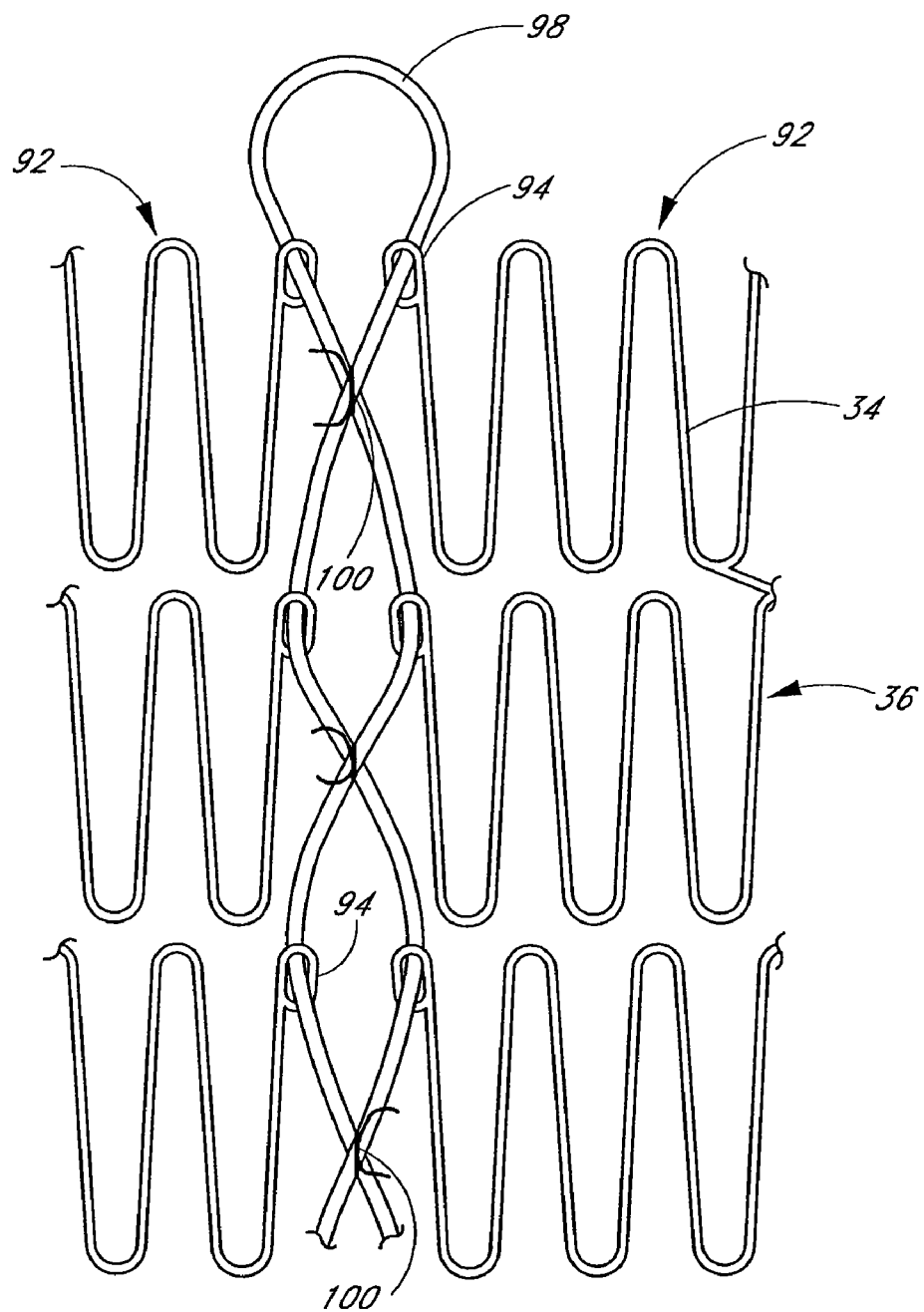
FIG. 12 is a close-up view of a portion of the harness of FIG. 11.

With reference next to FIGS. 11 and 12, a portion of an embodiment of a cardiac harness 90 is shown. These drawings show a method and apparatus for connecting adjacent panels 92 of a cardiac harness. As shown, each of the adjacent spring hinge panels 92 has several strands 36 of spring hinges 34. An eyelet 94 is disposed at an end of each strand, at the side edges 96 of each panel 92. In the illustrated embodiment, a line 98 of suture material, such as Pebax™, is threaded through the eyelets 94 in order to connect the adjacent panels 92 to one another. Adjacent panels 92 are effectively laced to one another by the Pebax suture line 98. The suture line crosses over itself at several points. Ties 100 preferably are applied at each of the crossover points in order to help maintain the positioning of the suture line 98.

Figure 13:
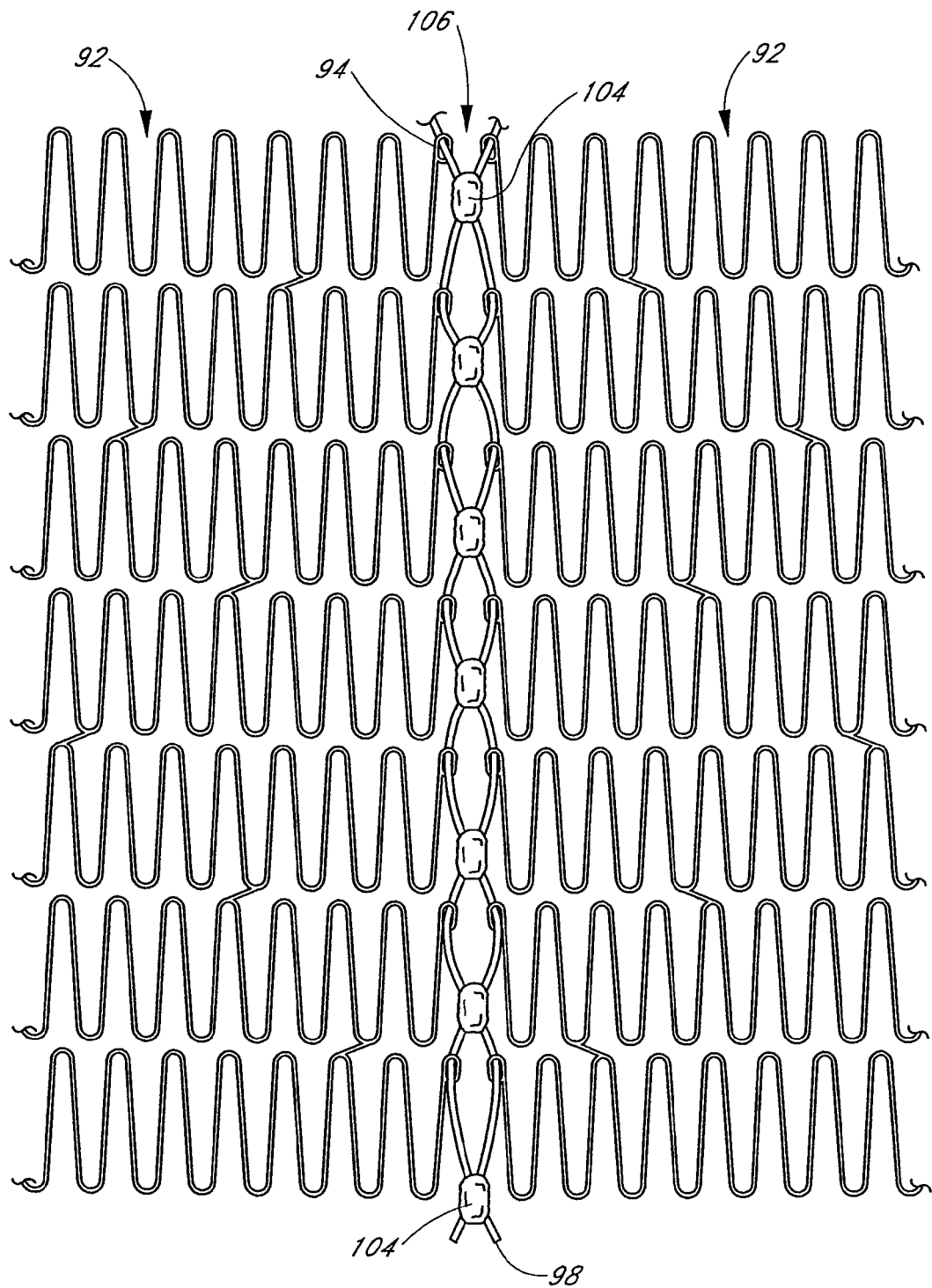
FIG. 13 shows a portion of yet a further embodiment of a cardiac harness.

FIG. 13 shows another method of holding the suture line 98 together at the crossover points wherein a block 104 of polymer material is heat-molded to the suture 98 line at each crossover point. This securely and predictively holds the suture line together, and accordingly more predictively holds the adjacent panels 92 to one another.

In the embodiments illustrated in FIGS. 11-13, adjacent spring hinge panels 92 are shown connected to one another without a panel of nonconductive material being placed therebetween. However, the adjacent spring hinge panels 92 are spaced from each other so as to be electrically discontinuous. As such, even if there is not a nonconductive panel arranged between spring hinge panels 92, a space 106 disposed between the panels 92 is acceptable for some embodiments.

Each of the spring hinge panels 92 shown in FIGS. 11-13 have been etched from a flat piece of material. As such, the eyelets 94 have been cut out of that material. In an embodiment wherein a wire is deformed to form the strands of spring hinges in each panel, eyelets can also be formed along the edges of the panel. Such eyelets can be formed using any conventional means, such as bending the wire back on itself or helically coiling the wire between strands of spring hinges. Further, in a panel constructed of rows of interwoven, overlapping strands of spring hinges, the ends of the panels may be at least partially folded over the panel so as to provide a connecting point or hook for a connector such as a suture line. Similarly, a suture line can be threaded through portions of the strands. It is to be understood that several types of materials, such as polyester mesh, cloth or the like can be threaded through eyelets, hooks, or other attachment media to connect adjacent spring hinge panels and/or to connect such panels to nonconductive panels.

Figure 14:
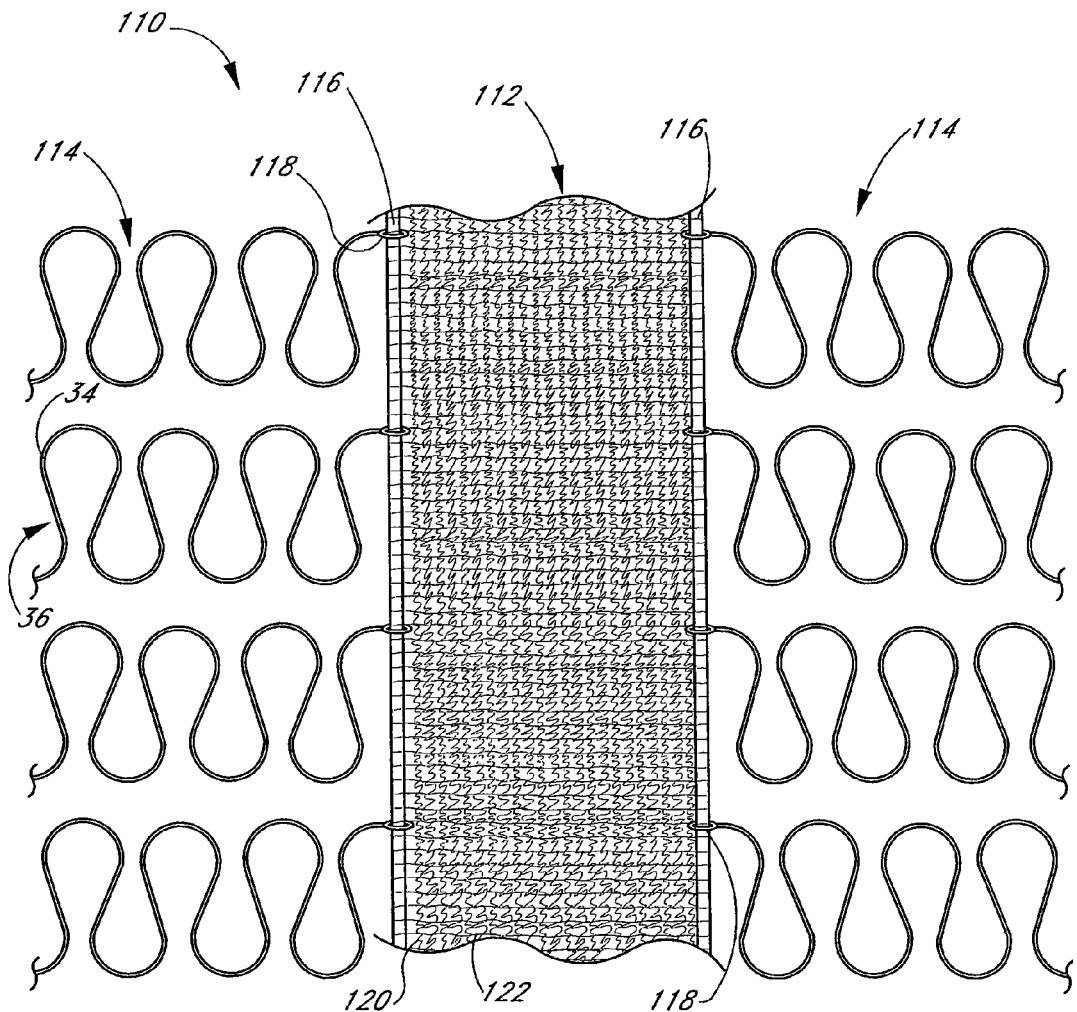
FIG. 14 shows a portion of yet another embodiment of a multi-panel cardiac harness.

With reference next to FIG. 14, another embodiment of a cardiac harness 110 is presented wherein a nonconductive panel 112 comprising a woven cloth is disposed between two spring hinge panels 114. The cloth panel 112 extends between a pair of elongate edge supports 116, which also engage the adjacent spring hinge panels 114. Preferably, the edge supports 116 each comprise a bar or pin that extends through eyelets 118 of the spring hinge strands 36. As such, the spring hinge panels 114 are free to rotate and move about the edge supports 116 and the nonconductive panel 112 is disposed between the spring hinge panels 114.

With continued reference to FIG. 14, the illustrated nonconductive cloth panel 112 is woven so as to have longitudinally extending fibers 120 and transversely extending fibers 122. The transversely extending fibers 122 are disposed in substantially the same direction as the strands 36 of spring hinges 34, which extend in a direction circumferentially about the heart. Preferably, the cloth 112 is relatively inelastic or has relatively low elasticity. When the heart expands, the transverse fibers 122 become taut, and expansion of the harness 110 is controlled by expansion of the spring hinges 34. When the heart is of reduced size, however, the transverse fibers 122 are flexible and move with the heart. In the illustrated embodiment, the longitudinal fibers 120, though relatively inelastic, are somewhat bunched together. Thus, if the heart grows longitudinally, the longitudinal fibers 120 will begin to straighten out, but will not restrain or constrain the longitudinal expansion of the heart. Preferably, the longitudinal fibers 120 are of such a length that their full expansion will not be reached in the operational range of the harness 110.

In the illustrated embodiment, the strands 36 of spring hinges 34 are connected to one another in a manner allowing relative movement between the rows or strands of spring hinges. As such, longitudinal expansion of the heart with little or no resistance is accommodated by all the panels of the harness.

In another embodiment, the cloth comprises relatively inelastic transverse fibers, yet relatively elastic longitudinal fibers. Thus, the cloth will elastically expand in a longitudinal direction, but not in a transverse direction.

In yet another embodiment, a cardiac harness comprises a plurality of spring hinge panels that are spaced apart from each other. Several strands of each spring hinge panel are each connected to a relatively inflexible and nonconductive bar or rod. The nonconductive bar or rod maintains the spring hinge panels at a specified distance from one another, thereby ensuring electrical discontinuity between spring hinge panels.

Figure 15:
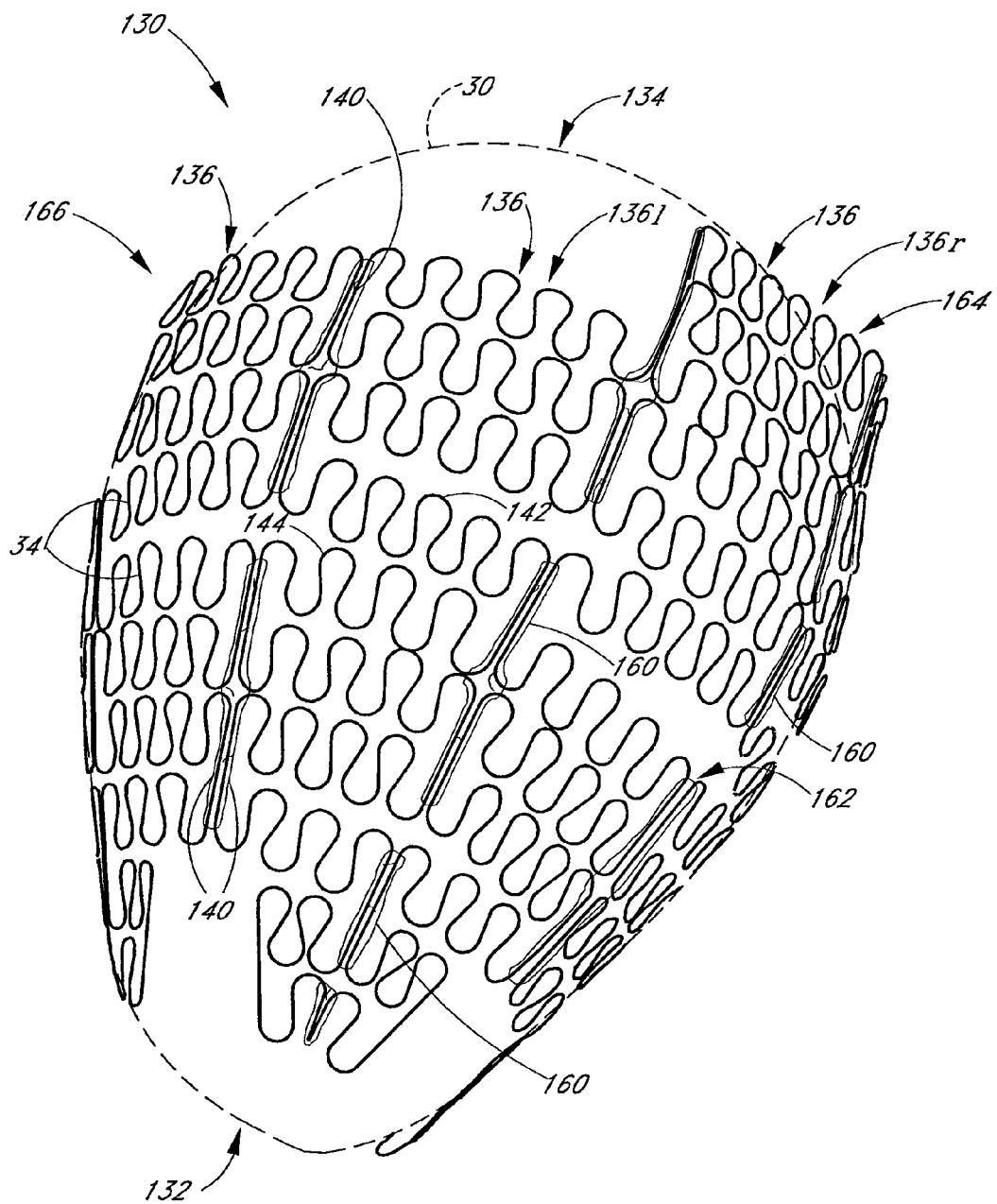
FIG. 15 is a schematic view of another embodiment of a cardiac harness, disposed on a schematically illustrated heart.

With next reference to FIG. 15, another embodiment of a cardiac harness 130 is shown disposed upon a simulated heart 30. As shown, the harness 130 extends longitudinally from an apex portion 132 to a base portion 134 of the heart 30. The harness 130 comprises a plurality of spring arrays 136 that are interconnected with one another such that the harness circumferentially surrounds the heart. Each spring array 136 comprises a plurality of spring elements or members 34 and a plurality of elongate portions 140. In the illustrated embodiment, the spring members 34 are substantially similar to the spring members 34 discussed above with reference to FIGS. 2A and 2B. As will be discussed below, the elongate portions 140 facilitate attaching each spring array 136 to adjacent spring arrays. Each spring array 136 preferably is formed of a metallic wire, preferably having a shape memory property, covered with a dielectric material. More preferably, the spring arrays 136 are formed of drawn Nitinol wire that is coated with silicone. Methods of manufacturing the spring arrays are discussed below with reference to FIGS. 28A through 29B.

Figure 16A:
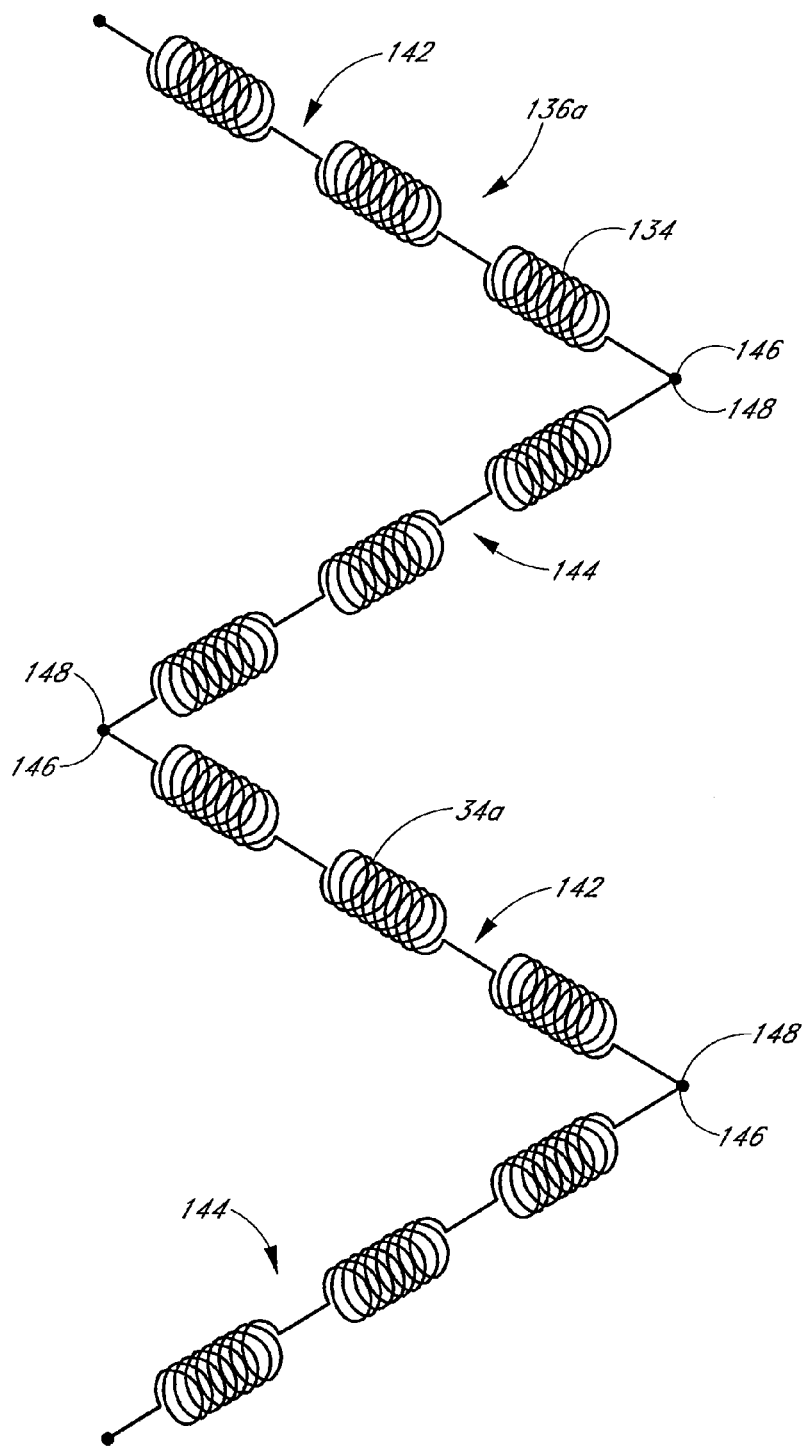
FIG. 16A is a functional representation of a spring array of the cardiac harness of FIG. 15.
Figure 16B:
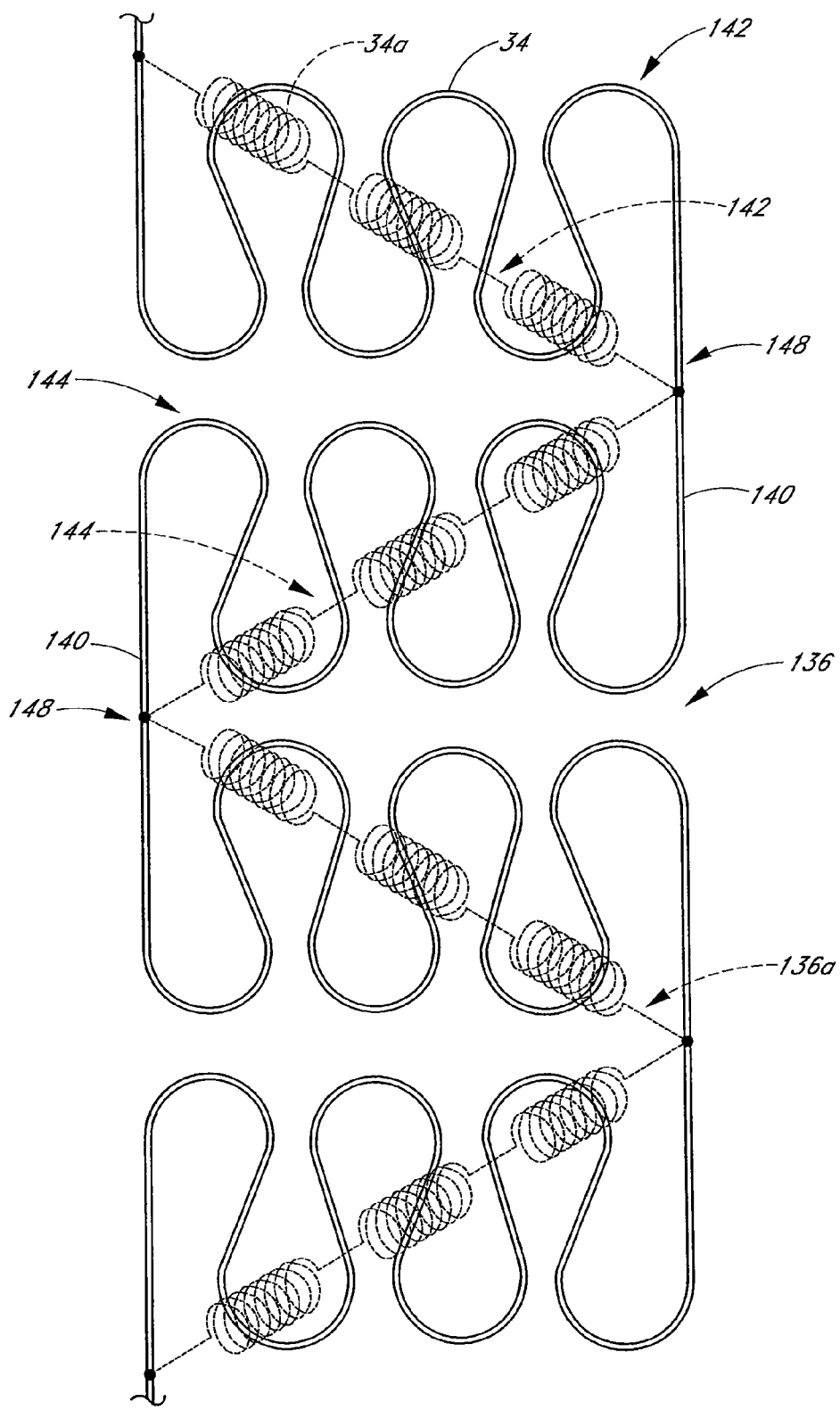
FIG. 16B shows a portion of a spring array of cardiac harness of FIG. 15 with the functional representation of FIG. 16A superimposed thereon.

With next reference to FIGS. 16A and 16B, each spring array 136 is generally "zigzag" shaped. As used herein, "zigzag" is a broad term and is used in its ordinary sense and refers, without limitation, to a series of turns, angles or alterations of course. FIG. 16A illustrates one embodiment of a spring array 136a which serves as a conceptual model emphasizing the zigzag shape of the spring arrays 136 of FIG. 15. As shown in FIG. 16A, the zigzag shape comprises a plurality of zig portions 142 interconnected with a plurality of zag portions 144. Each of the zig portions 142 and zag portions 144 comprises a plurality of interconnected spring elements 34a. As used herein, "zig" is a broad term and is used in its ordinary sense and refers, without limitation, to one of the sections of a zigzag course which is typically at an angle relative to a zag, but may also be substantially parallel. Likewise, as used herein, "zag" is a broad term and is used in its ordinary sense and refers, without limitation, to one of the sections of a zigzag course which is typically at an angle relative to a zig, but may also be substantially parallel. Preferably, a zig is connected to a zag at their respective ends 146. In an additional embodiment, the ends 146 of a zig and zag can be joined by a connector. As such, connected zigs and zags can be integrally formed or separately formed in alternative embodiments. Furthermore, the interconnections of the zig portions with the zag portions comprise a plurality of discrete locations 148 whereby the spring array can be attached to other spring arrays. In the illustrated embodiment, the discrete locations 148 are depicted as points of connection 148 for a zig portion 142 and a zag portion 144. It is to be understood that, in other embodiments, discrete locations 148 can be elongate.

FIG. 16B illustrates a portion of one embodiment of a spring array 136. The dashed lines depict the schematic zigzag shape of the spring array 136a. It will be appreciated that the spring array 136 illustrated in FIG. 16B is substantially functionally similar to the spring array 136a illustrated in FIG. 16A, but the spring array 136 of FIG. 16B comprises a plurality of spring members substantially similar to the spring members 34 illustrated in FIG. 15. As further shown in FIG. 16B, the above-discussed discrete locations 148 are disposed in or on a plurality of elongate portions 140 interconnected with the spring members 34.

Figure 17:
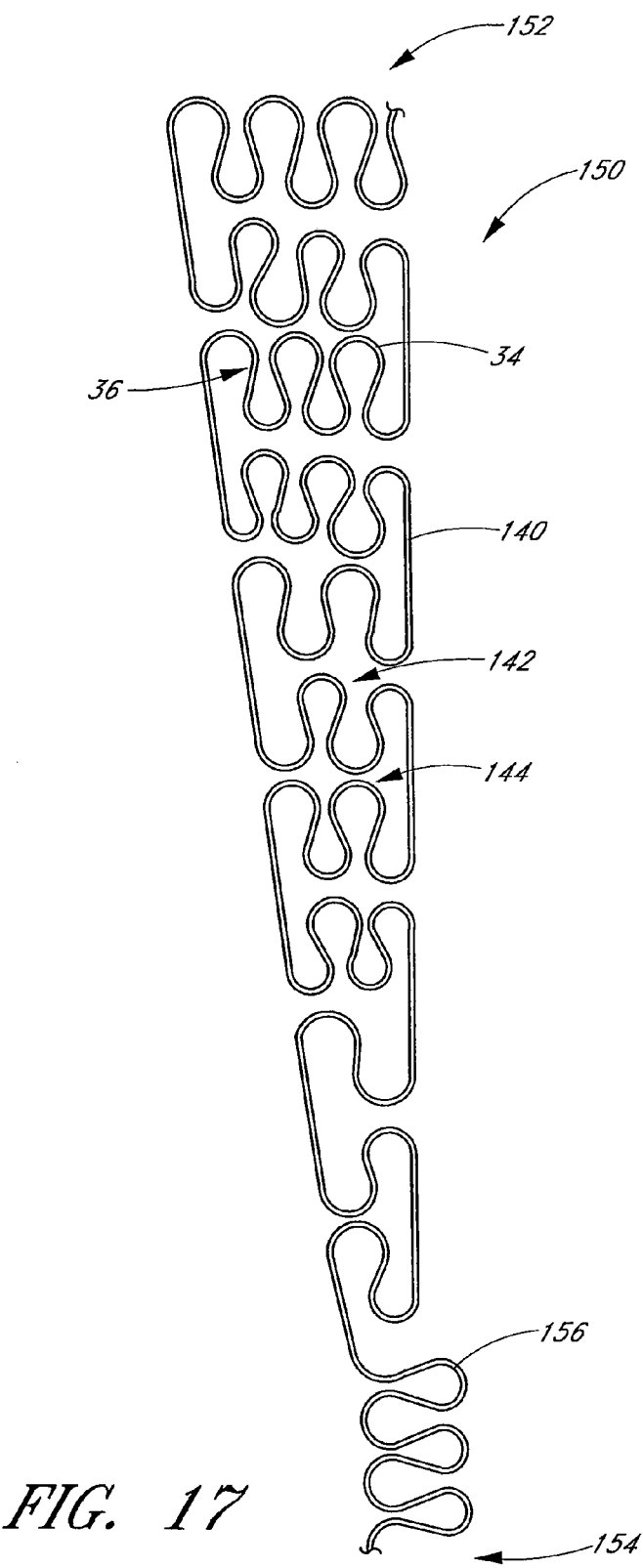
FIG. 17 illustrates a schematic view of another embodiment of a spring hinge array for use in connection with a cardiac harness.

FIG. 17 illustrates a preferred embodiment of a spring array 150 for use in an embodiment of a cardiac harness. The spring array 150 shown in FIG. 17 is similar to the spring arrays 136 illustrated in FIGS. 15 and 16B. However, the spring array 150 of FIG. 17 is shaped somewhat differently. For example, the FIG. 17 array 150 has a decreasing number of spring members 34 in successive rows 36 passing from a base end 152 to an apex end 154. This decrease in the number of spring members 34 tapers the width of the spring array 150 such that the assembled cardiac harness also tapers and thus better conforms to the general anatomy of the heart.

In the embodiment illustrated in FIG. 17, a plurality of longitudinal spring members 156 are included at the apex end 154 of the spring array 150. The longitudinal spring members 156 facilitate attaching the apex end 154 of the spring array 150 to the ends of other spring arrays so as to enclose the cardiac harness around the apex portion of the heart. When the cardiac harness is installed on a heart, the longitudinal spring members 156 from adjacent spring arrays 150 may overlap one another. However, the longitudinal spring members remain very compliant. This arrangement allows significant motion of the apex of the heart in any direction with very little, if any, resistance from the harness. In order to help maintain the position of the harness on the heart, one or more stitches can optionally be applied to the heart at the apex in order to hold the overlapping spring members in place.

With reference again to the embodiment shown in FIG. 15, elongate portions 140 of each spring array 136 are attached to corresponding elongate portions 140 of each adjacent spring array 136 by a dielectric material 160, such as an adhesive, silicone, or other similar material. Preferably, the elongate portions 140 are attached to one another such that there is a space 162 between each pair of elongate portions 140, as shown in FIG. 15. The space 162, as well as the dielectric cover on the metallic wire, electrically isolates each spring array 136 from the other spring arrays in the harness 130. This arrangement ensures that there is no electrical continuity circumferentially about the harness 130. Thus, if defibrillator paddles or electrodes are applied to a harness that is placed on the patient's heart, the electric current created between the paddles is not conducted around the heart through the harness, but instead passes through the heart. As such, the effectiveness of the defibrillating paddles is not defeated by the presence of the harness.

With continued reference to FIG. 15, a right side 164 of the cardiac harness 130 comprises longitudinally longer spring arrays 136 containing more rows 36 of spring members 34 than do the spring arrays on a left side 166 of the harness 130. As such, the harness extends higher on the right side of the heart than on the left side of the heart. Due to the anatomy of the human heart, the right atrium extends further from the apex of the heart than does the left atrium. The cardiac harness 130 illustrated in FIG. 15 fits about the uppermost portion of the right atrium where the atrium begins to curve inwardly and also fits about the uppermost portion of the left atrium. As such, the harness 130 fits better and is held more securely on the heart than if the right side of the harness were configured the same as the left side.

The harness 130 illustrated in FIG. 15 is configured so that no spring members 34 overlap one another. As such, wear of the harness due to repeated flexing and relative movement of the spring members 34 is avoided.

As discussed briefly above, the cardiac harness 130 of FIG. 15 has a dielectric coating. The dielectric coating is configured to prevent an electric field applied by defibrillator paddles from being communicated by the metallic harness. As such, the electric field passes through the heart with little or no diminishment by the harness.

In the illustrated embodiment, the dielectric coating comprises silicone rubber. However, it is to be understood that various materials and methods can be used to coat the harness with dielectric material. For example, in one embodiment, an etched harness is coated with a layer of Parylene™, which is a dielectric polymer available from Union Carbide. Other acceptable materials include silicone rubbers, urethanes, and ceramics, as well as various polymers and the like. The materials can be applied to an etched harness by various methods, such as dip coating and spraying.

In accordance with one embodiment, a cardiac harness preferably is formed into a desired shape before being coated with dielectric material. For example, in one embodiment, Nitinol wire preferably is first treated and shaped to develop a shape memory of a desired spring member structure. Silicone tubing is then pulled over the wire. The wire then is returned to its shape memory shape. In another embodiment, Nitinol wire is dip coated with an insulating material. A preferred method for insulating a wire is discussed in more detail below with reference to FIGS. 28A through 29B.

In another embodiment, a harness is electrically insulated by stretching an extruded tube of flexible dielectric material over the harness. In a further embodiment, another flexible dielectric tube is disposed on the opposite side of the harness to effectively sandwich the harness between layers of flexible expandable dielectric material. Gaps may be formed through the dielectric material to help communicate the electric field through the harness to the heart.

Figure 18:
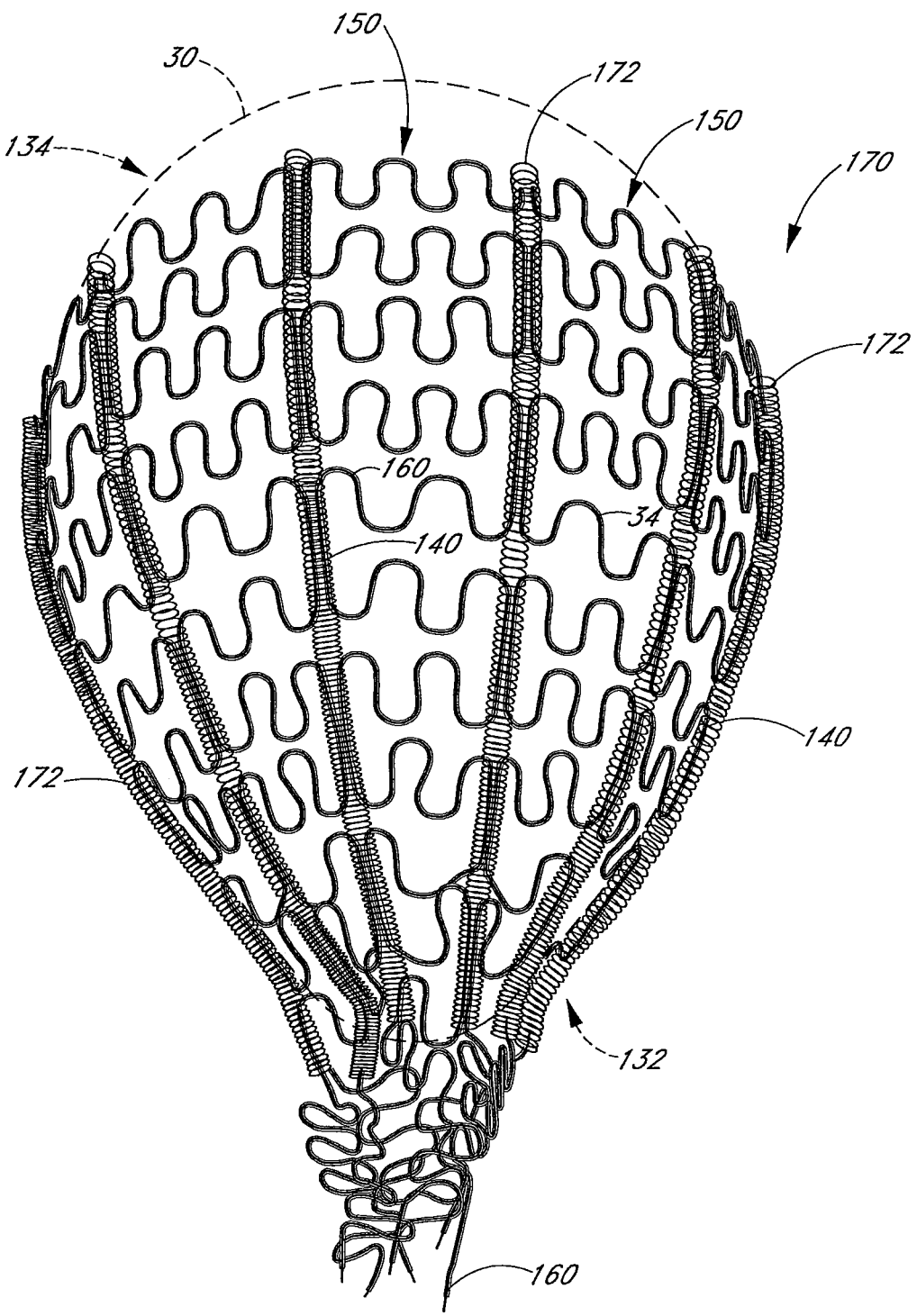
FIG. 18 is a schematic view of another embodiment of a cardiac harness employing several of the spring arrays of FIG. 17 and being disposed on a schematically illustrated heart.

FIG. 18 illustrates another embodiment of a cardiac harness 170 for reducing cardiac wall tension. The cardiac harness 170 is shown disposed upon a simulated heart 30. As shown, the harness 170 extends longitudinally from a base portion 134 to an apex portion 132 of the heart. The harness 170 comprises a plurality of spring arrays 150 that are attached to one another such that the harness circumferentially surrounds the heart. The spring arrays 150 of the harness illustrated in FIG. 18 are substantially similar to the spring array 150 illustrated in FIG. 17. As such, each spring array comprises a plurality of spring elements or members 34, a plurality of elongate portions 140 (see FIGS. 15-16B) and a plurality of longitudinal spring members 156. Furthermore, each spring array 150 shown in FIG. 18 is generally zigzag shaped (FIGS. 16A-16B) and comprises a plurality of zig portions interconnected with a plurality of zag portions. The interconnections of the zig portions with the zag portions comprise a plurality of discrete locations whereby each spring array is attached to other spring arrays.

As shown in FIG. 18, each spring array 150 is attached to adjacent spring arrays by elongate coils 172. In the illustrated embodiment, each elongate coil 172 is wound onto two adjacent spring arrays 150 such that the respective elongate portions 140 of the spring arrays are surrounded by windings of the coil 172. Because each spring array is coated with dielectric material 160, each spring array 150 is electrically isolated from the other spring arrays in the harness 170 and from the coils 172. This arrangement ensures that there is no electrical continuity circumferentially about the harness. Thus, if defibrillator paddles are applied to a harness 170 that is placed on the patient's heart, the electric current created between the paddles is not conducted around the heart through the harness. Instead, the electric current passes through the heart, and the effectiveness of the defibrillating paddles is not defeated by the presence of the harness.

In accordance with yet another embodiment, selected ones of the elongate coils 172 of the cardiac harness 170 depicted in FIG. 18 are electrically connected to an electronic controller or the like. In this manner, the coils can be used as electrodes for a defibrillator, pacemaker or the like.

Figure 19:
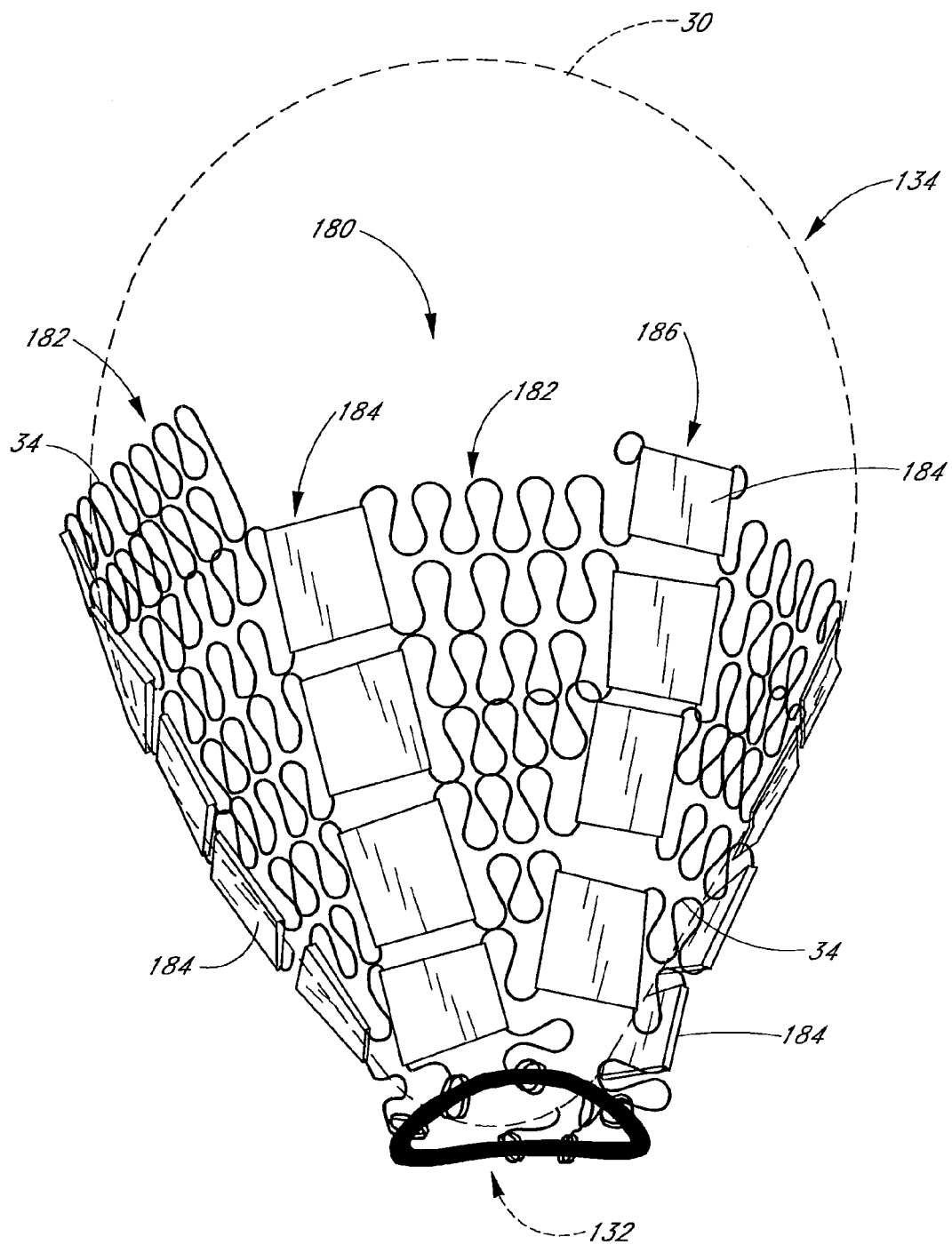
FIG. 19 is a schematic view of yet another embodiment of a cardiac harness, shown disposed upon a schematically illustrated heart.

FIG. 19 illustrates another embodiment of a cardiac harness 180 disposed upon a simulated heart 30. As shown, the harness extends longitudinally from a base portion 152 to an apex portion 154 of the heart. The harness 180 comprises a plurality of spring arrays 182 that are attached to one another such that the harness circumferentially surrounds the heart 30. The spring arrays 182 illustrated in FIG. 19 have a zigzag structure similar to the spring arrays 136 illustrated in FIGS. 15 and 16B. Thus, each spring array 182 is comprised of a plurality of spring members 34, a plurality of elongate portions 140 and at least one longitudinal spring member 156.

As shown in FIG. 19, each spring array 182 is attached to adjacent spring arrays 182 by a plurality of nonconductive connectors 184. In the illustrated embodiment, each nonconductive connector 184 comprises a layer of polymer that is connected to the elongate portions 140 of adjacent spring arrays 182 by adhesive or other mode of connection. Preferably, each connector 184 is generally inelastic or has relatively low elasticity so that the elastic expansion and contraction of the harness 180 is generally controlled by the properties of the spring arrays 182. It is contemplated that the nonconductive connectors 184 may comprise any medical grade polymer such as, but not limited to, polyethylene, polypropylene, polyurethane, nylon, PTFE and ePTFE. Of course, in additional embodiments, at least some of the connectors 184 can be formed of an elastic material that contributes to the mild circumferential force applied to the heart 30 by the harness 180.

With continued reference to FIG. 19, the nonconductive connectors 184 define a space 186 between adjacent spring arrays 182. As such, each spring array 182 is electrically isolated from the other spring arrays 182 in the harness 180 by the space 186. This arrangement provides no electrical continuity circumferentially about the harness 180. Thus, if defibrillator paddles are applied to a harness that is placed on the patient's heart, the electric current created between the paddles is not conducted around the heart through the harness. Instead, the electric current passes through the heart, and the effectiveness of the defibrillating paddles is not defeated by the presence of the harness.

In the harness embodiment 180 illustrated in FIG. 19, the spring arrays 182 are not coated with a dielectric material. It is to be understood, however, that some or all of the spring arrays 182 may be coated with a dielectric in order to further diminish any electrical continuity around the heart.

Figure 20:
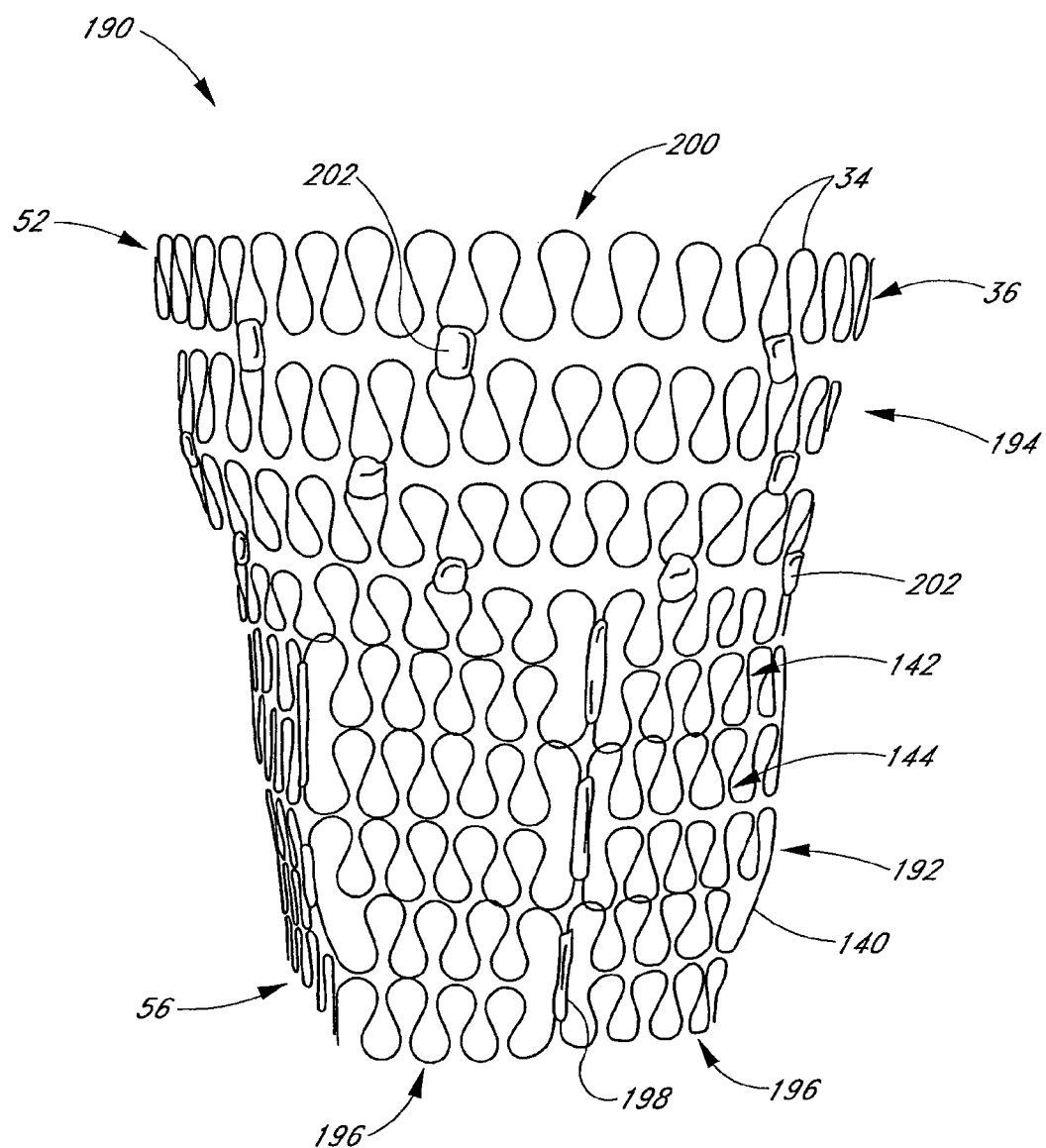
FIG. 20 is a schematic view of still another embodiment of the cardiac harness.

FIG. 20 illustrates another embodiment of a cardiac harness 190 for reducing cardiac wall tension. The cardiac harness 190 is configured to circumferentially surround a patient's heart and extends longitudinally from a base end 52 to an apex end 56. The harness of FIG. 20 comprises a first portion 192 and a second portion 194.

The first portion 192 is configured to be disposed closer to the apex portion of the heart than the second portion 194, and comprises a plurality of spring arrays 196. The first portion 192 spring arrays 196 illustrated in FIG. 20 share similarities with the spring arrays 136 illustrated in FIGS. 15 and 16B, in that each spring array 196 in the first portion 192 comprises a plurality of spring members 34 interconnected with a plurality of elongate portions 140. Furthermore, each first portion spring array 196 is generally zigzag shaped and comprises a plurality of zig portions 142 interconnected with a plurality of zag portions 144.

As shown in FIG. 20, the elongate portions 140 of each first portion spring array 196 are attached to corresponding elongate portions 140 of adjacent spring arrays 196 by a nonconductive bond 198, such as an adhesive, silicone rubber or other similar material. In the illustrated embodiment, the elongate portions 140 are attached to one another such that a dielectric layer 198 is disposed between each pair of elongate portions 140. Also, each array 196 is coated with a dielectric coating. As such, each spring array 196 is electrically isolated from the other spring arrays in the harness, and there is no electrical continuity circumferentially about the first portion 192 of the harness 190.

Continuing with reference to FIG. 20, the second portion 194 of the cardiac harness 190 comprises a plurality of circumferentially extending rings 200 disposed longitudinally adjacent to one another. Each ring 200 comprises a plurality of interconnected spring elements or members 34 covered with a dielectric material. The spring members 34 shown in FIG. 20 are substantially similar to the spring members 34 discussed above with reference to FIGS. 2A and 2B. A plurality of nonconductive connectors 202 interconnects adjacent rings 200, and also interconnects the second portion 194 and first portion 192 of the harness 190. Preferably, the nonconductive connectors 202 are formed of a semi-compliant material, such as silicone rubber or other similar material. More preferably, the connectors 202 are formed of the same material used for the dielectric coating.

Figure 21:
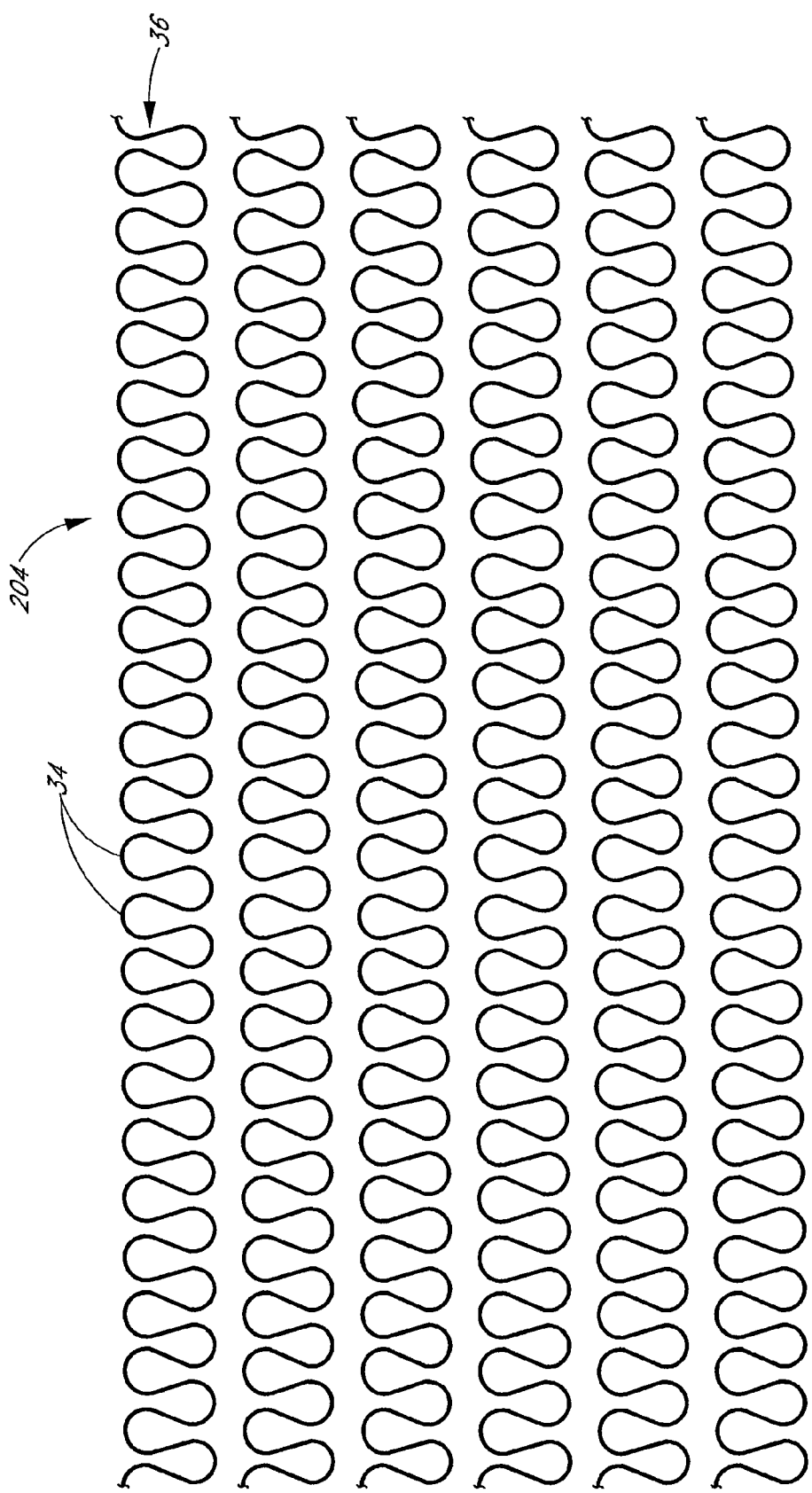
FIG. 21 shows several strips or rows of spring hinges prior to being formed into a harness.

In one embodiment, each ring 200 is formed by first forming an elongate series 204 of spring members, several of which are depicted in FIG. 21, and then joining the opposite ends of the series 204 together to form the ring-shaped configuration 200 shown in FIG. 20. It will be appreciated that the lengths of the elongate series 204 are selected such that the resulting rings 200 are sized in conformity with the general anatomy of the patient's heart. More specifically, some rings 200 have more spring members 34 than others.

Figure 22:
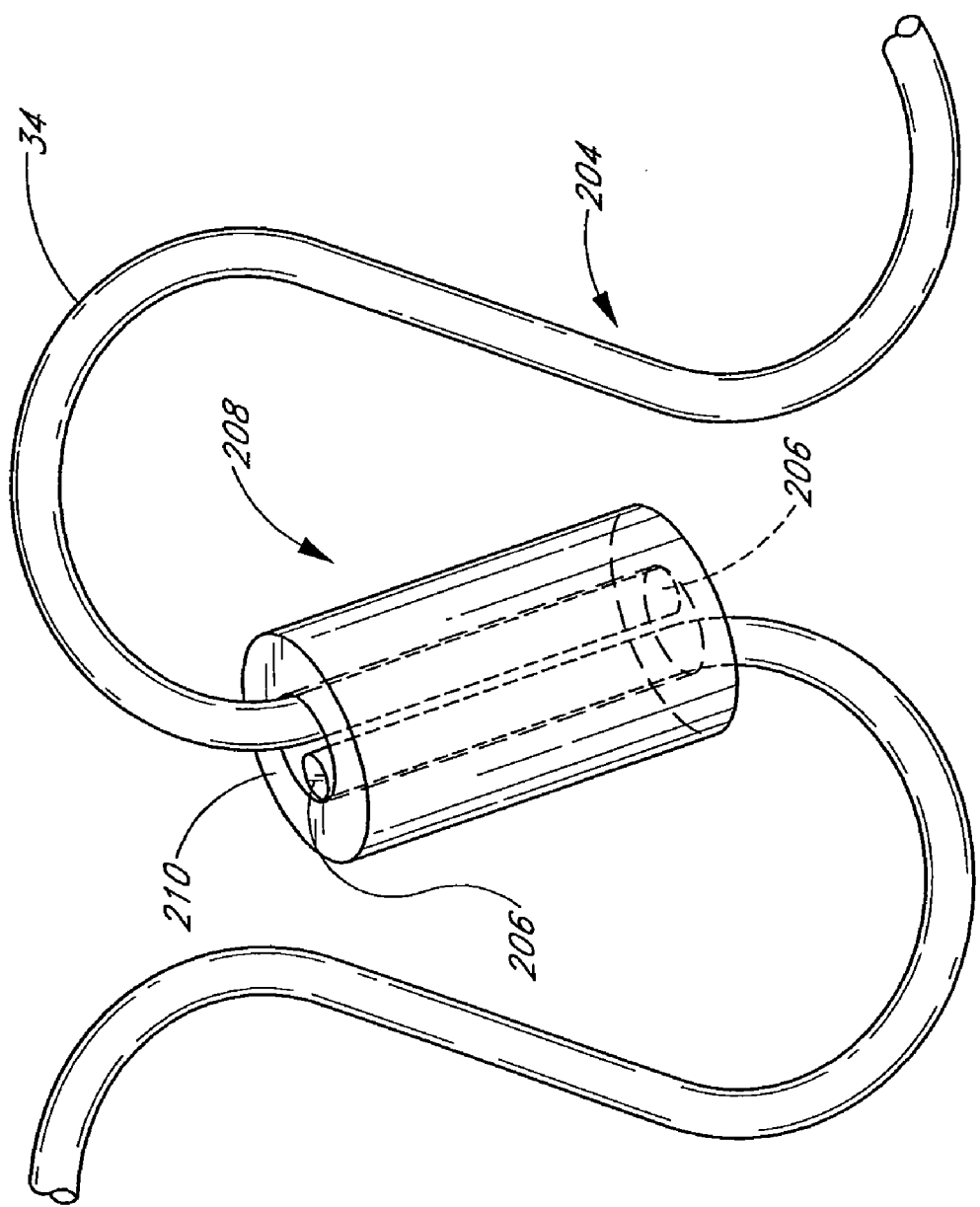
FIG. 22 illustrates a connective junction where opposing ends of a strand of spring hinges are connected in accordance with one embodiment.

With reference next to FIG. 22, the opposite ends 206 of each circumferentially extending ring 200 preferably are attached to one another by a connective junction 208. In the illustrated embodiment, each connective junction 208 comprises a small tube segment 210 into which the opposite ends 206 of the ring 200 are inserted. The tube segment 210 serves to prevent the opposite ends 206 of the ring from tearing loose from one another after the harness is placed on the heart. Preferably, each tube segment 210 is filled with a dielectric material such as silicone, or other similar material after the ring-ends 206 are placed therein.

In the embodiment illustrated in FIGS. 20, the rings 200 in the second portion 194 are configured to be circumferentially stiffer than the attached arrays 196 in the first portion 192. As such, the harness 190 has a firmer grip about the base portion of the patient's heart. This arrangement helps anchor the harness securely onto the heart.

It will be appreciated that because the rings 200 are coated with dielectric material and are interconnected by a nonconductive material, each ring is electrically insulated from the other rings in the second portion 194 of the harness 190, as well as from the first portion 192 of the harness. This arrangement ensures that there is no electrical continuity either circumferentially about the harness 190 or longitudinally across the harness. As such, when defibrillator paddles are applied to a harness that is placed on the patient's heart, the electric current created between the paddles is not conducted around the heart through the harness, but rather travels through the heart. Thus the effectiveness of the defibrillating paddles is not defeated by the presence of the harness.

In a still further embodiment, two or more of the spring arrays 196 in the first portion 192 are not coated with a dielectric, but are connected to a controller configured to selectively electrically charge the arrays 196. In this manner, the arrays 196 function as electrodes for a defibrillator, pacemaker or the like. At least one pair of the non-coated electrode-arrays preferably are insulated from one another by a dielectric-covered array. As such, current flowing between the electrode-arrays is forced to flow through the heart rather than through the rest of the harness.

Figure 23:
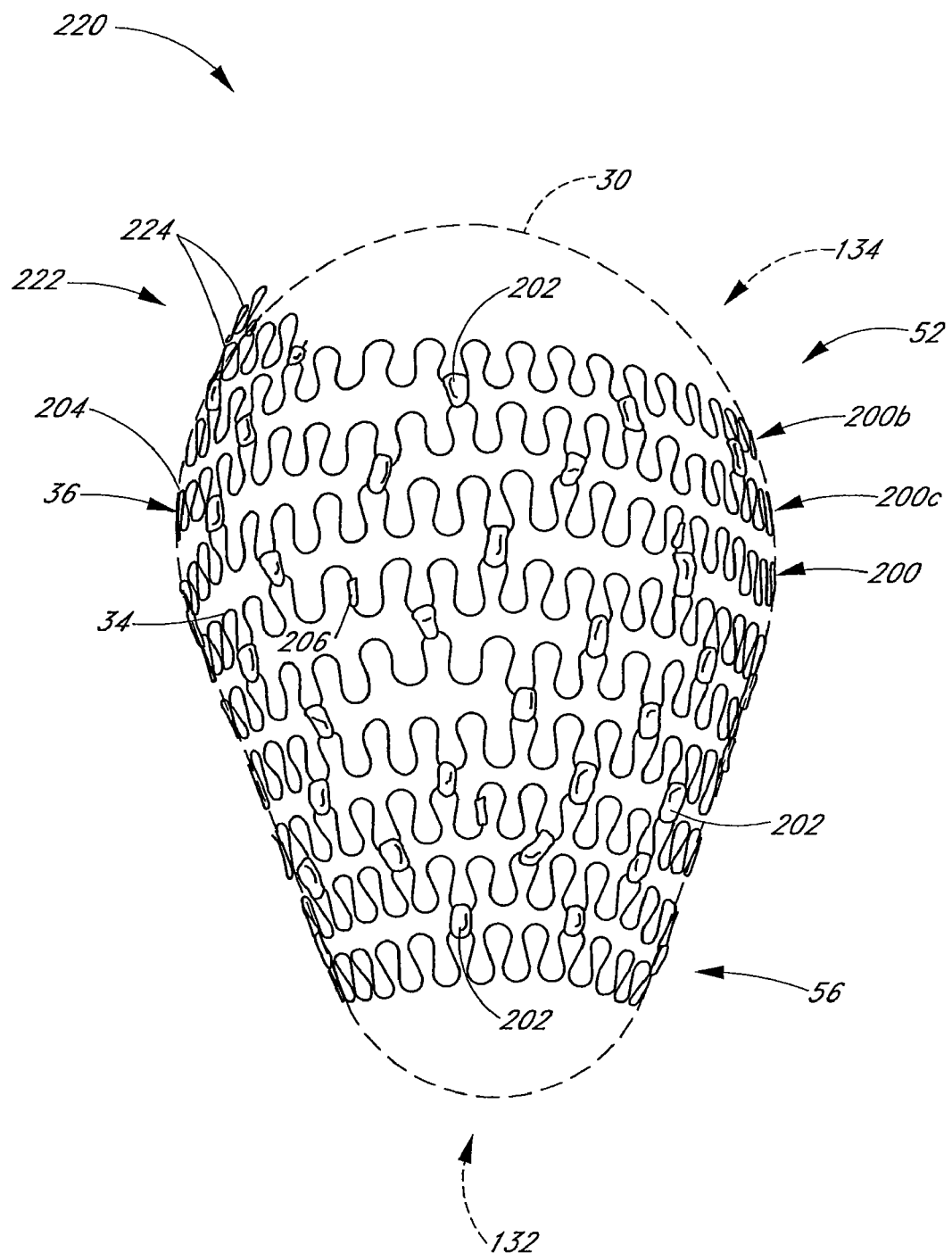
FIG. 23 is a schematic view of a still further embodiment of a cardiac harness, shown disposed upon a schematically illustrated heart.

With next reference to FIG. 23, another embodiment of a cardiac 220 harness is illustrated disposed on a schematically illustrated heart 20. As shown, the cardiac harness 220 is configured to circumferentially surround the heart and extend longitudinally from a base portion 134 to an apex portion 132 of the heart. The harness 220 comprises a plurality of circumferentially extending rings 200 disposed longitudinally adjacent to one another. Each ring 200 comprises a plurality of interconnected spring members 34 covered with a dielectric material. The spring members 34 shown in FIG. 23 are substantially similar to the spring members 34 discussed above with reference to FIGS. 2A and 2B. A plurality of nonconductive connectors 202 interconnects adjacent rings 200. The nonconductive connectors 202 have a length oriented longitudinally relative to the rings so as to create space between adjacent rings. Preferably, the nonconductive connectors are formed of a semi-compliant material, such as silicone or other similar material.

In one embodiment, each ring 200 initially comprises an elongate strand 36, as shown in FIG. 21. Each elongate strand is comprised of a series 204 of the above-discussed spring members 34. During manufacturing of the cardiac harness 220, each elongate strand is cut to a length such that when opposite ends of the elongate strand are bonded together, the elongate strand assumes the ring-shaped configuration shown in FIG. 23. With reference again to FIG. 22, the opposite ends 206 of each circumferentially extending ring 200 are attached to one another by a connective junction 208.

It will be appreciated that the lengths of the elongate strands 36 are selected such that the resulting rings 206 are sized in conformity with the general anatomy of the patient's heart. More specifically, strands in the apex portion of the harness are not as long as the strands used to form the base portion. As such, the harness generally tapers from the base toward the apex in order to generally follow the shape of the patient's heart. In another embodiment, the diameter of a ring 200b at the base of the harness is smaller than the diameter of the adjacent ring 200c. In this embodiment, the harness has a greatest diameter at a point between the base and apex ends, and tapers from that point to both the base and apex ends. Preferably, the point of greatest diameter is closer to the base end 52 than to the apex end 56. It is contemplated that the lengths of the strands, as well as the sizes of the spring members, may be selected according to the intended size of the cardiac harness 220 and/or the amount of compressive force the harness is intended to impart to the patient's heart.

With continued reference to FIG. 23, the right side 222 of the base portion 52 of the harness 220 comprises strands 224 of interconnected spring members that are not configured into a ring, but extend only partially about the circumference of the harness 220. Preferably, the partial strands 224 are connected to the adjacent full ring in a manner so that the partial strands are stretched. As such, the partial strands 224 will bend inwardly to "cup" the upper portion of the right atrium, as simulated in FIG. 23.

It will be appreciated that because the rings 200 are coated with dielectric material and are interconnected by nonconductive material 202, each ring is electrically isolated from the other rings in the harness. As such, there is no electrical continuity either circumferentially about the harness 220 or longitudinally along the harness. Thus, if defibrillator paddles are applied to a harness that is placed on the patient's heart, the electric current flowing between the paddles passes through the heart rather than being conducted around the heart through the harness. As a result, the effectiveness of the defibrillating paddles is not defeated by the presence of the harness.

Figure 24:
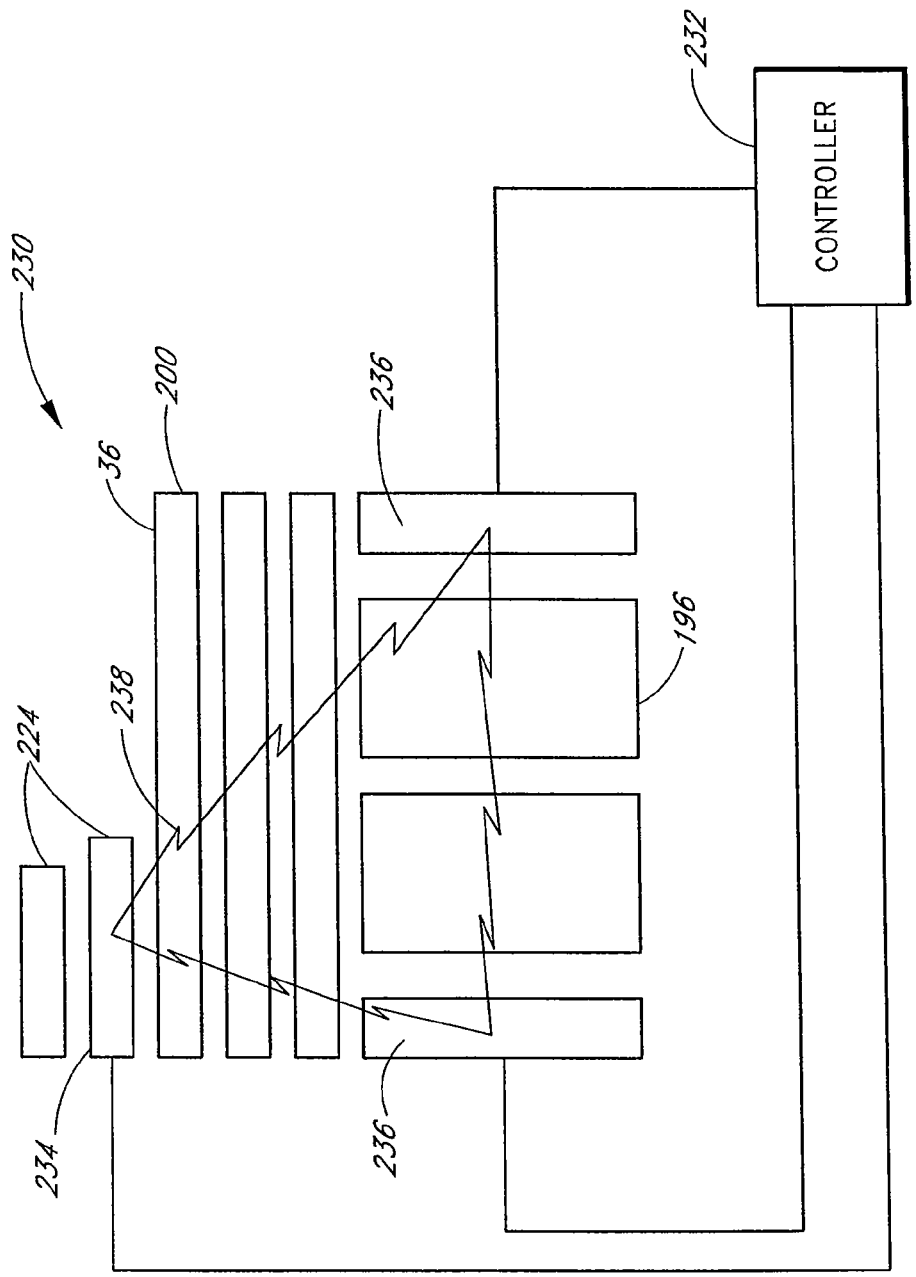
FIG. 24 schematically illustrates a cardiac harness having several electrodes connected to a controller.

In a still further embodiment, an embodiment having a first and second portion 192, 194, as in the harness 190 embodiment depicted in FIG. 20, further includes at least one partial strand 224 as just discussed with reference to FIG. 23. With reference next to FIG. 24, a cardiac harness 230 embodiment is illustrated schematically wherein one of two partial strands 224 is not covered with a dielectric material, but is electrically connected to a controller 232 and, similarly, two of the spring arrays 236 are connected to the controller 232 and are not electrically insulated from the heart. As such, the non-coated partial strand 234 and non-coated spring arrays 236 function as electrode members for a defibrillator or pacemaker. In accordance with one embodiment, the controller 232 energizes the electrode members 234, 236 in a manner to create a generally triangular electric field 238 between the electrodes 234, 236 so as to facilitate defibrillation.

Figure 25:
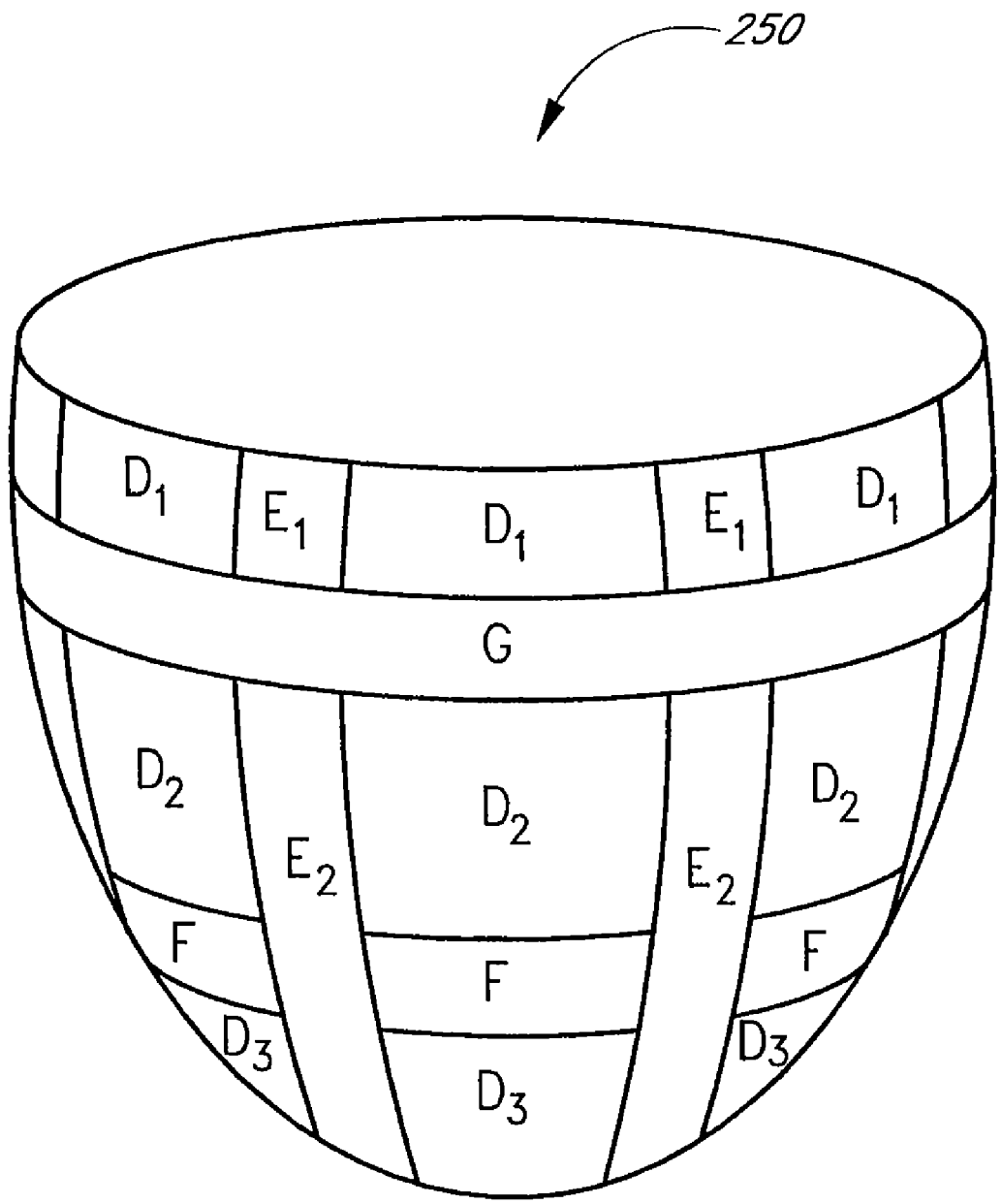
FIG. 25 schematically illustrates yet another embodiment of a cardiac harness having multiple panels.

With reference next to FIG. 25, another embodiment of a multipanel cardiac harness 250 is shown schematically in order to represent versatility in multipanel harness design. Several spring hinge panels $D_1$ are disposed circumferentially around the harness 250, but are separated from one another by nonconductive panels $E_1$ interposed therebetween. Several second spring hinge panels $D_2$ are also disposed circumferentially around the harness. These second spring hinge panels are spaced from each other by second nonconductive panels $E_2$ disposed therebetween. In a similar manner, several third spring hinge panels $D_3$ are disposed circumferentially about the harness 250 but are electrically isolated from one another by the second nonconductive panels $E_2$, which are spaced therebetween.

As shown in FIG. 25, the first, second and third spring hinge panels $D_1$, $D_2$, $D_3$ are longitudinally aligned with one another, but are longitudinally electrically isolated from each other by further nonconductive panels F, G, interposed therebetween. For example, several nonconductive panels F are disposed between adjacent second and third spring hinge panels $D_2$, $D_3$. Nonconductive panel G extends circumferentially all the way around the harness 250. The circumferential nonconductive panel G also is disposed longitudinally between the first and second spring hinge panels $D_1$, $D_2$.

The embodiment shown in FIG. 25 is configured to disrupt the flow of electricity both circumferentially around the harness 250 and longitudinally from one end of the harness to the other. As with the embodiments discussed above, the nonconductive panels can be constructed of many different types of materials. In one embodiment, the circumferential nonconductive panel G is constructed of an elastic material. In another embodiment, panel G is constructed of a non-elastic but flexible material that is folded or bunched together so as to allow circumferential expansion of the harness. Further, it is to be understood that the non-conductive panels F, G may be formed of different materials having different properties. For example, panel G may be more elastic than panels F. In a similar manner, at least some of the spring hinge panels $D_1$, $D_2$, $D_3$, may exhibit different elastic properties.

In accordance with a still further embodiment, the spring hinge panels are formed of a Nitinol tubing. Holes are formed through the tubing at selected locations. The tubing has a very small diameter such as, for example, less than about 0.5 millimeters. As discussed above, sometimes an implantable medical device such as a pacemaker can be helpful in monitoring and stimulating a patient's heart. Such a pacemaker typically has electrical leads arranged on a portion of the heart wall. Sometimes scar tissue can form around the leads. The scar tissue has a negative impact on heart function and can reduce the effectiveness of the electrical charge provided by the leads. Accordingly, it is desired to reduce the formation of scar tissue about pacemaker leads. One way of reducing scar tissue is to supply medicaments such as steroids to the tissue adjacent the leads. In the present embodiment, a harness constructed at least partially out of small diameter tubing is arranged so that the holes through the tubing are disposed near or adjacent a pacemaker lead or other implantable medical device. The tubing is attached to a source of medicaments such as steroids. Medicaments are delivered through the tubing to the site of anticipated scar tissue buildup. Additionally, the small diameter of the tubing can dictate that the medicament is delivered very slowly over time in order to achieve desirable results.

Figure 26:
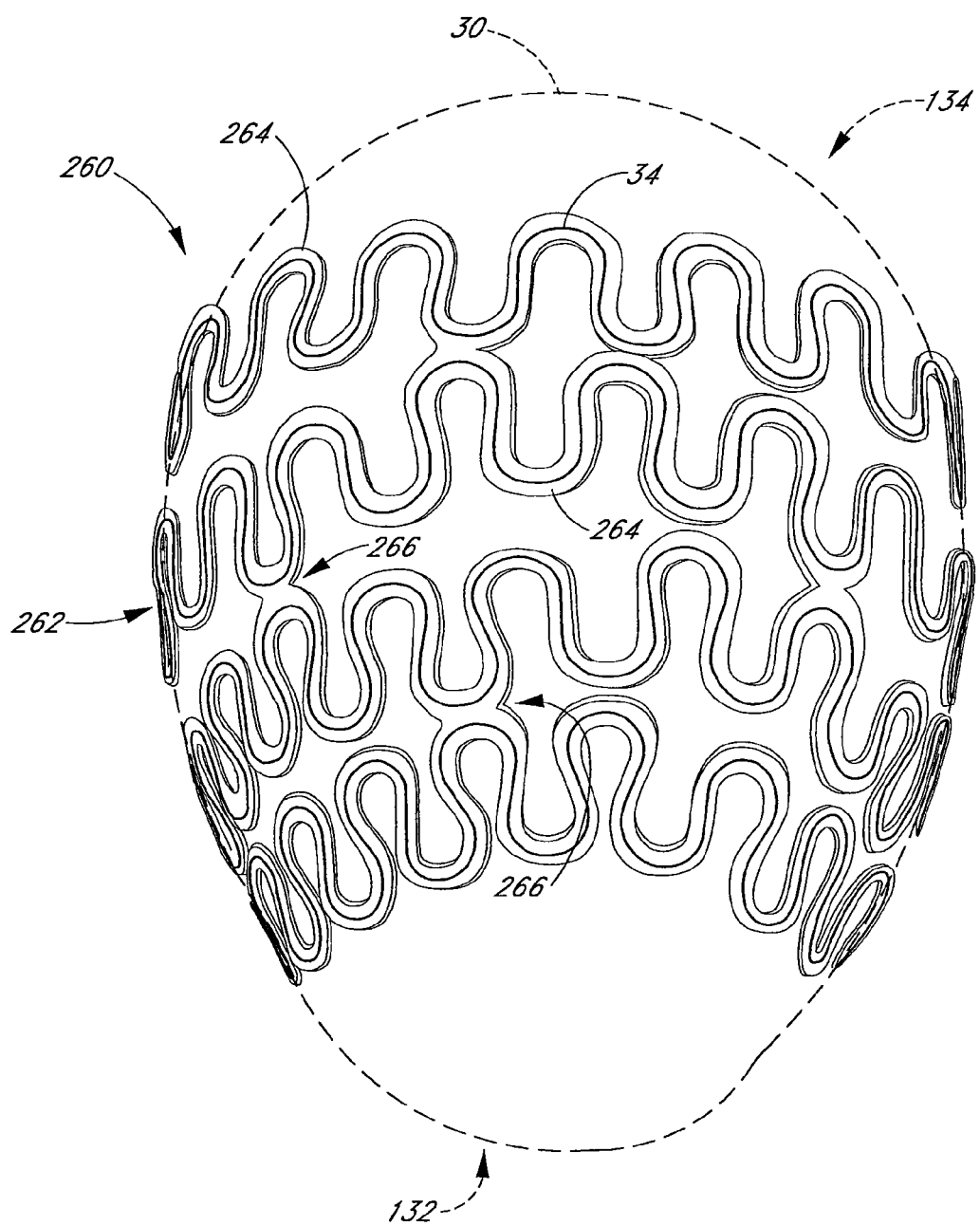
FIG. 26 illustrates still another embodiment of a cardiac harness disposed on a schematically represented heart.

FIG. 26 illustrates another embodiment of a cardiac harness 260 disposed on a simulated heart 30. As shown, the cardiac harness 260 is configured to circumferentially surround the heart and extends longitudinally from a base portion 134 to an apex portion 132 of the heart 38. The harness 260 comprises a plurality of circumferentially extending rings 262. Each ring 262 comprises a plurality of interconnected spring members 34 covered with a dielectric material 264. The spring members 34 shown in FIG. 26 are substantially similar to the spring members 34 discussed above with reference to FIGS. 2A and 2B. A plurality of nonconductive connectors 266 interconnects adjacent rings 262. The nonconductive connectors 266 are formed of the dielectric material 264 which covers the spring members 34.

In one embodiment, each ring 262 initially comprises an elongate strand 36, as discussed above with reference to FIG. 21A. Each elongate strand is comprised of a series 204 of the above-discussed spring members. During manufacturing of the cardiac harness 260, each elongate strand is cut to a length such that when opposite ends of the elongate strand are secured together, the elongate strand assumes the ring-shaped configuration shown in FIG. 26. The lengths of the elongate strands are selected such that the resulting rings 262 are sized in conformity with the general anatomy of the patient's heart. In one embodiment, the lengths of the strands, as well as the sizes of the spring members, are selected according to the intended size of the cardiac harness 260 and/or the amount of compressive force the harness is intended to impart to the patient's heart.

Once the elongate strands are formed into the ring-shaped configuration shown in FIG. 12, the rings 262 are covered with a dielectric material 264. The dielectric covering is configured to prevent an electric current applied by defibrillator paddles from being communicated by the rings of the harness. As such, the electric current passes through the heart with little or no diminishment by the harness.

Various materials and methods can be used to coat the harness with dielectric material. In the illustrated embodiment, the rings are coated with silicone rubber. Other acceptable materials include Parylene™, urethanes, and ceramics, as well as various polymers and the like. The materials can be applied to a harness by various methods, such as dip coating and spraying, or any other suitable method.

In the illustrated embodiment, the rings 262 are placed on a mandrel and coated with dielectric material 264. It is contemplated that such a mandrel has an exterior surface configured such that the resulting ring structure is sized in conformity with the general anatomy of a human heart. Excess dielectric material 264 is then removed from the cardiac harness, such that the shape of the dielectric material generally follows the shape of the spring members, as shown in FIG. 12. In this embodiment, excess dielectric material is left intact between some of the spring members of adjacent rings so as to provide the nonconductive connectors 266 between adjacent rings 262. The excess dielectric material may be removed from the harness by using any cutting tool, such as a scalpel, laser, water jet, or the like.

Figure 27:
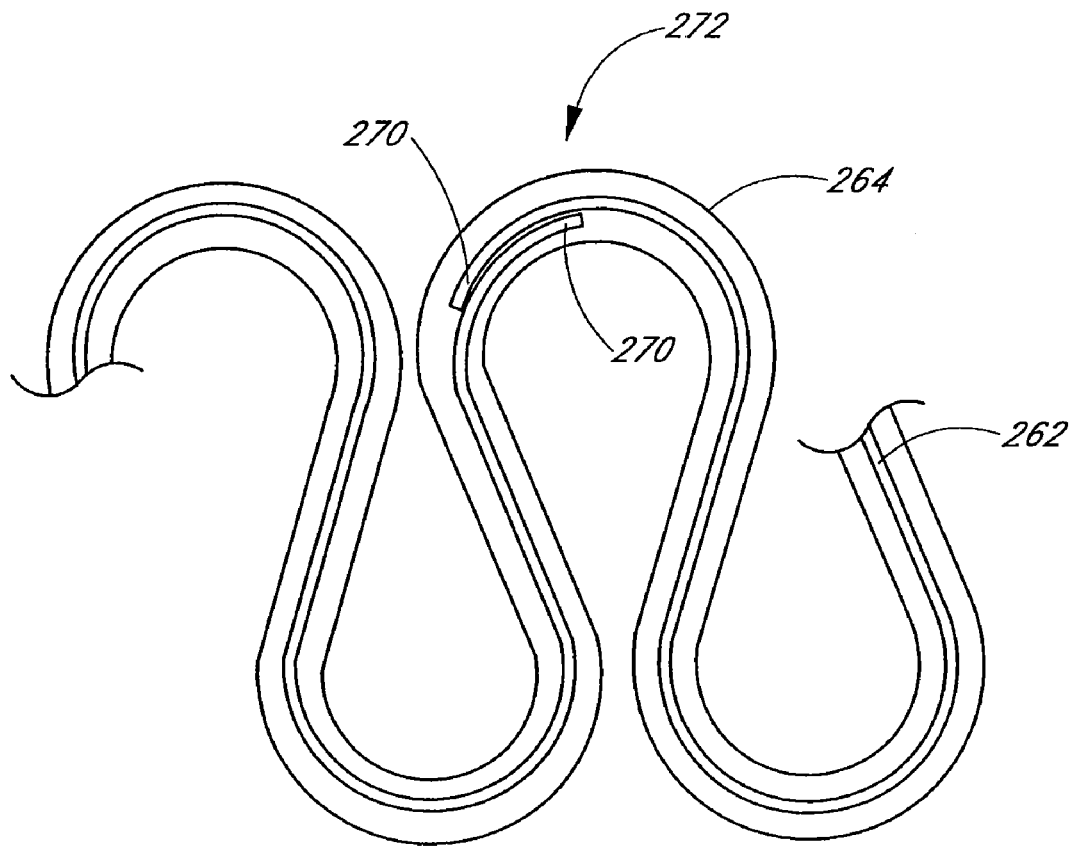
FIG. 27 is a close-up representation of a portion of the harness of FIG. 26.

A connective junction joins 272 opposite ends 270 of each circumferentially extending ring 262. With reference next to FIG. 27, the material comprising the dielectric cover 264 preferably secures the opposite ends 270 of the rings. In another embodiment, the opposite ends 270 of each ring may be further secured by applying silicone, or another. similar material, before the dielectric cover 264 is applied to the harness. Also, the opposing ends may be welded, soldered, adhesively bonded, or held together by other means. In still another embodiment, the connective junctions may each comprise a small tube segment into which the opposite ends of the ring are inserted prior to application of the dielectric sheet to the harness.

Figures 28A, 28B:
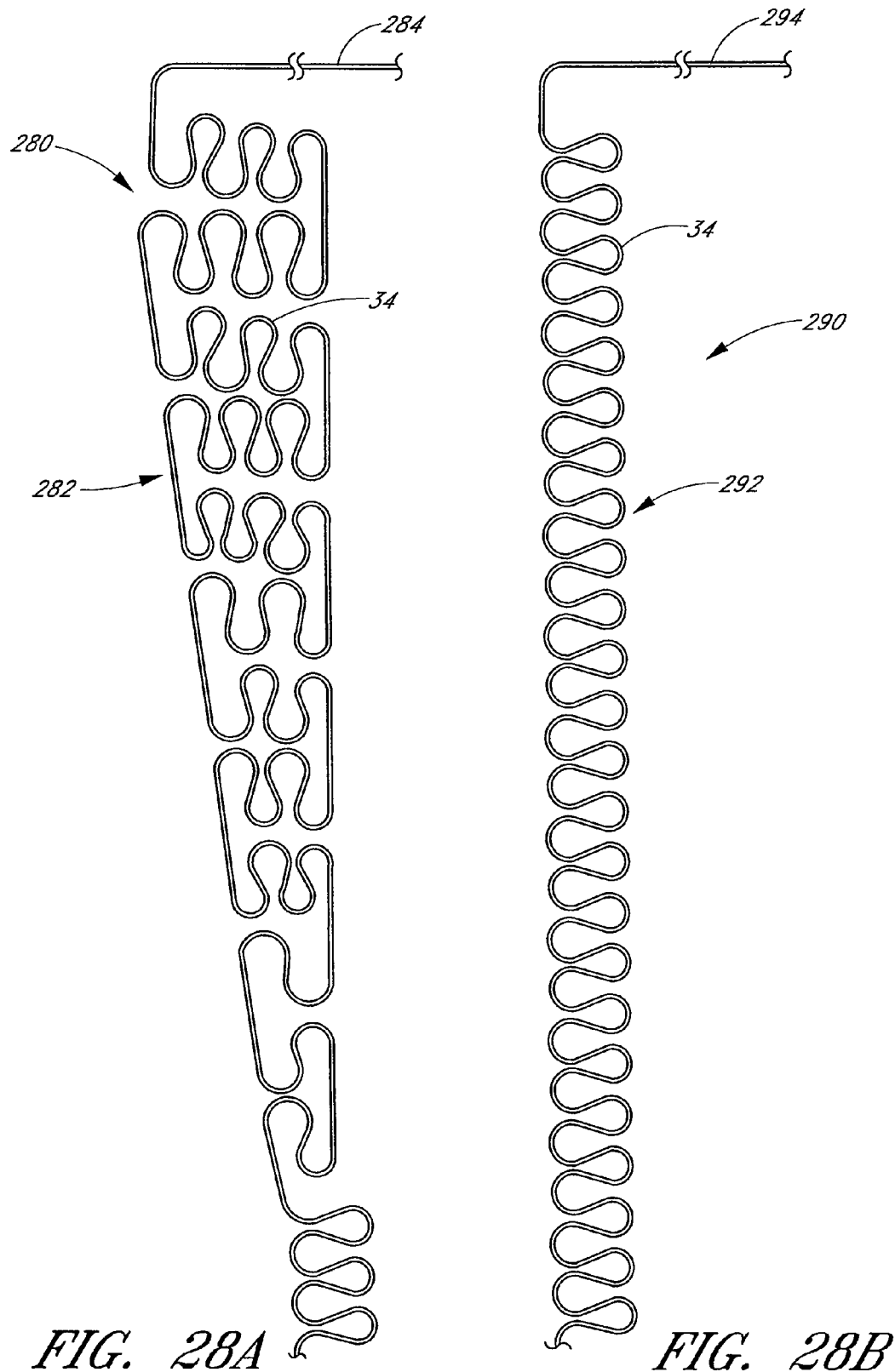
FIG. 28A shows an embodiment of a spring hinge array.
FIG. 28B shows an embodiment of a strand of spring hinges.

A method of manufacturing a cardiac harness is now described with reference to FIGS. 28A through 29B. The method generally comprises configuring a metallic wire, and then covering the wire with an electrically insulative material. FIGS. 28A and B depict embodiments wherein Nitinol wire is first treated and shaped to develop a "remembered" shape 280, 290 comprising a harness portion 282, 292 and a leader portion 284, 294. The harness portion 282, 292 is comprised of a plurality of spring members 34 that are preferably arranged into a predefined configuration, such as the spring array 282 illustrated in FIG. 28A or the elongate strand 292 shown in FIG. 28B. In one embodiment, while held in the predefined configuration, the harness portion 282, 292 is heat-set at a suitable temperature to establish the shape memory. The wire is then electropolished in accordance with standard methods known in the art. As shown in FIGS. 28A and 28B, the wire is configured such that the leader portion 284, 294 is disposed at one end of the harness portion 282, 292 of the wire.

Once the harness portion of the wire is configured as described above, the wire is then covered with an electrically insulative material. In one embodiment, a tube of dielectric material is pulled over the wire as discussed below. Preferably the tube is formed of silicone rubber. It will be appreciated that the inner diameter of the tube determines the level of tightness between the tube and wire. In one embodiment, wherein the wire has a diameter of about 0.012 inches, a silicone tube having an inner diameter of about 0.012 inches provides a relatively tight fit. In another embodiment, wherein the wire has a diameter of about 0.012 inches, a silicone tube having an inner diameter of about 0.020 inches provides a relatively loose fit. A silicone tube having an inner diameter smaller than the diameter of the wire can also be used to obtain a snug fit. In a preferred embodiment, silicone tubing sold under the trademark Nusil MED 4755 is used.

FIGS. 29A and B illustrate an apparatus 300 and method for drawing a silicone rubber tube 302 over a harness portion 282. For purposes of example, the strand portion 290 of FIG. 28B is depicted in the apparatus 300 of FIGS. 29A and B. The apparatus 300 comprises a clamp 304 into which one end of the harness portion 292 is secured. The leader portion 294 of the strand portion 290 preferably is free. A pressure source 306 supplies a solvent 308 under a substantially constant pressure of, preferably, less than about 5 atmospheres and, more preferably, between about 1 to 2 atmospheres. The pressure source 306 supplies the solvent 308 to a connector 310 which comprises a Y-shaped adapter 312. The solvent is supplied to one of the Y branches 314, another of the Y branches 316 includes a compression valve, such as a Touhyborst valve. Preferably, a hollow needle 320 extends from a base portion 322 of the Y adapter 312.

With particular reference to FIG. 29A, the silicone tube 302 preferably is threaded over the outer diameter of the hollow needle 320. As such, solvent 308 is supplied through the needle 320 to the tube 302. In one embodiment, the solvent primarily comprises a lubricant which facilitates sliding the tube over wire. Preferably, the lubricant is comprised of DOW OS-10, isopropyl alcohol (IPA), or another similar substance. In another embodiment, the solvent comprises a substance which primarily swells the inner diameter of the tube so as to facilitate sliding the tube over the wire. In such an embodiment, the solvent preferably comprises hexane, heptane, xylene, and the like.

With continued reference to FIG. 29A, once the solvent is flowing within and through the silicone tube 302, the free end of the leader portion 294 is threaded into the tube 302 and the tube 302 is advanced over the leader 292 until the entire leader portion is disposed in the tube. With reference next to FIG. 29B, once the leader portion 292 has been advanced completely through the tube 302, the leader portion 292 is threaded through the hollow needle 320 and through the Touhy-borst valve 316 of the Y adapter. The free end 324 of the leader portion 292 is then clamped in place.

Due to the tortuous path defined by the spring elements 34, it may be difficult for the tubing 302 to be slid over the harness portion 292 without deforming the spring elements 34. However, in accordance with one embodiment, and with the assistance of the solvent, the tubing 302 is drawn over the harness portion 292 taking care not to substantially stretch the spring members. In accordance with another embodiment, the wire 290 is pulled straight and held tightly in place between the clamps 304. In this manner, it is quite easy to advance the tubing 302 over the harness portion 292 because the spring elements 34 of the harness portion have been substantially straightened out, as illustrated in FIG. 29B. Once the tubing is disposed completely over the harness portion 292, the clamps 304 are released and, due to the shape memory and superelastic properties of Nitinol, the harness portion 292 springs back substantially to its shape memory configuration.

In accordance with a still further embodiment, once the free end 324 of the leader 294 has been clamped, the entire wire is stretched so that the spring elements 34 of the harness portion 292 are partially deformed, but are not stretched straight. In this manner, it becomes relatively easy to slide the tubing over the spring elements 34 of the harness portion, but the spring elements are not deformed so much as to compromise their preformed memory shape. In this embodiment, care is taken to further deform the spring elements as little as possible while sliding the tubing into place.

In each of these embodiments, once the tube has reached the end of the wire, and thus is covering the entire harness portion 292, the supply of pressurized solvent 308 is stopped and the solvent supply apparatus 306 is removed. The ends of the wire are removed from the clamps 304 and the leader portion 294 is trimmed from the harness portion 292. The harness portion substantially assumes its shape memory shape, and is ready to be further formed into a cardiac harness.

In order to relieve localized stresses that may exist between the tubing and the wire, the tubing/wire combination preferably is exposed to low level vibrations in order to help the tubing relax and shrink to a relaxed condition on the wire. In a preferred embodiment, the tubing/wire combination is treated with an ultrasonic cleaner which ultrasonically vibrates the combination. Such vibration can be termed "micromotion", and helps the tubing and wire achieve a state of equilibrium relative to one another. As such, localized stresses that may have formed as the tubing was advanced over the wire are relaxed.

Although this invention has been disclosed in the context of several preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

We claim:

1. A cardiac harness configured to fit about a patient's heart, the harness comprising:
    a plurality of conductive panels, each of the panels being spaced from an adjacent panel so that there is no electrical continuity between the conductive panels, and a panel disposed between each two adjacent conductive panels.

2. The cardiac harness of claim 1, wherein the panel is non-conductive.

* * * * *